(12) United States Patent
Greenhalgh

(10) Patent No.: US 10,285,820 B2
(45) Date of Patent: May 14, 2019

(54) FIXATION DEVICE AND METHOD

(71) Applicant: Stout Medical Group, L.P., Quakertown, PA (US)

(72) Inventor: E. Skott Greenhalgh, Gladwyne, PA (US)

(73) Assignee: Stout Medical Group, L.P., Quakertown, PA (US)

( * ) Notice: Subject to any disclaimer, the term of this patent is extended or adjusted under 35 U.S.C. 154(b) by 0 days.

(21) Appl. No.: 15/442,449

(22) Filed: Feb. 24, 2017

(65) Prior Publication Data

US 2017/0165083 A1  Jun. 15, 2017

Related U.S. Application Data

(63) Continuation of application No. 14/703,704, filed on May 4, 2015, which is a continuation of application
(Continued)

(51) Int. Cl.
*A61F 2/44* (2006.01)
*A61F 2/46* (2006.01)
*A61F 2/30* (2006.01)

(52) U.S. Cl.
CPC .......... *A61F 2/442* (2013.01); *A61F 2/30771* (2013.01); *A61F 2/447* (2013.01); *A61F 2/4425* (2013.01); *A61F 2/4611* (2013.01); *A61F 2002/3008* (2013.01); *A61F 2002/3052* (2013.01); *A61F 2002/3055* (2013.01); *A61F 2002/3093* (2013.01); *A61F 2002/30387* (2013.01); *A61F 2002/30448* (2013.01); *A61F 2002/30492* (2013.01); *A61F 2002/30507* (2013.01); *A61F 2002/30515* (2013.01); *A61F 2002/30523* (2013.01); *A61F 2002/30579* (2013.01); *A61F 2002/30777* (2013.01); *A61F 2002/30904* (2013.01); *A61F 2002/443* (2013.01); *A61F 2002/4475* (2013.01); *A61F 2002/4629* (2013.01); *A61F 2002/4677* (2013.01); *A61F 2220/005* (2013.01); *A61F 2220/0025* (2013.01);
(Continued)

(58) Field of Classification Search
CPC .................................................. A61F 2/44–447
USPC ........................................... 623/17.11–17.16
See application file for complete search history.

(56) References Cited

U.S. PATENT DOCUMENTS 646,119 A   3/1900  Clamer et al.
4,204,531 A 5/1980  Aginsky
(Continued)

FOREIGN PATENT DOCUMENTS

DE   19710392   7/1999
EP   0734702    10/1996
(Continued)

OTHER PUBLICATIONS

Choi, G. et al., "Percutaneous Endoscopic Lumbar Discemtomy by Transiliac Approach," *Spine*, 34(12):E443-446, May 20, 2009.
(Continued)

*Primary Examiner* — Nicholas J Plionis
(74) *Attorney, Agent, or Firm* — Levine Bagade Han LLP

(57) ABSTRACT

An implantable orthopedic stability device is disclosed. The device can have a contracted and an expanded configuration. A method of using the device between adjacent vertebral body surfaces for support and/or fixation of either or both of the adjacent vertebrae is also disclosed.

11 Claims, 29 Drawing Sheets

Related U.S. Application Data

No. 12/693,394, filed on Jan. 25, 2010, now abandoned, which is a continuation-in-part of application No. 12/617,663, filed on Nov. 12, 2009, now Pat. No. 9,408,708.

(60) Provisional application No. 61/113,691, filed on Nov. 12, 2008.

(52) U.S. Cl.
CPC .............. *A61F 2230/0082* (2013.01); *A61F 2250/0098* (2013.01); *A61F 2310/00976* (2013.01)

(56) References Cited

U.S. PATENT DOCUMENTS

| | | |
|---|---|---|
| 4,541,423 A | 9/1985 | Barber |
| 4,569,338 A | 2/1986 | Edwards |
| 4,636,217 A | 1/1987 | Ogilvie et al. |
| 4,653,489 A | 3/1987 | Tronzo |
| 4,716,893 A | 1/1988 | Fischer et al. |
| 4,725,264 A | 2/1988 | Glassman |
| 4,733,665 A | 3/1988 | Palmaz |
| 4,759,769 A | 7/1988 | Hedman et al. |
| 4,763,644 A | 8/1988 | Webb |
| 4,863,476 A | 9/1989 | Shepperd |
| 4,886,062 A | 12/1989 | Wiktor |
| 4,911,718 A | 3/1990 | Lee et al. |
| 4,932,975 A | 6/1990 | Main et al. |
| 4,941,466 A | 7/1990 | Romano |
| 4,969,888 A | 11/1990 | Scholten et al. |
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,192,327 A | 3/1993 | Brantigan |
| 5,217,483 A | 6/1993 | Tower |
| 5,258,031 A | 11/1993 | Salib et al. |
| 5,306,278 A | 4/1994 | Dahl et al. |
| 5,324,295 A | 6/1994 | Shapiro, III |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | Mckay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,895,387 A | 4/1999 | Guerrero et al. |
| 5,902,475 A | 5/1999 | Trozera et al. |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 5,993,483 A | 11/1999 | Gianotti |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,158 A | 6/2000 | Lin |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,619 A | 8/2000 | Truebe et al. |
| 6,102,950 A | 8/2000 | Vaccaro |
| 6,113,628 A | 9/2000 | Borghi |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |
| 6,132,465 A | 10/2000 | Ray et al. |
| 6,140,452 A | 10/2000 | Felt et al. |
| 6,146,417 A | 11/2000 | Ischinger |
| 6,159,244 A | 12/2000 | Suddaby |
| 6,159,245 A | 12/2000 | Meriwether et al. |
| 6,168,616 B1 | 1/2001 | Brown |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |
| 6,224,607 B1 | 5/2001 | Michelson |
| 6,235,043 B1 | 5/2001 | Reiley et al. |
| 6,241,734 B1 | 6/2001 | Scribner et al. |

(56) References Cited

U.S. PATENT DOCUMENTS

| | | |
|---|---|---|
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,296,644 B1 | 10/2001 | Saurat et al. |
| 6,302,914 B1 | 10/2001 | Michelson |
| 6,332,895 B1 | 12/2001 | Suddaby |
| 6,371,989 B1 | 4/2002 | Chauvin et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | Cox et al. |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |
| 6,514,255 B1 | 2/2003 | Ferree |
| 6,520,991 B2 | 2/2003 | Huene |
| 6,533,817 B1 | 3/2003 | Norton et al. |
| 6,551,342 B1 | 4/2003 | Shen et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Cragg |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 6,988,710 B2 | 1/2006 | Igarashi |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,452,371 B2 | 11/2008 | Pavcnik et al. |
| 7,488,337 B2 | 2/2009 | Saab et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,625,395 B2 | 12/2009 | Mückter |
| 7,628,807 B2 | 12/2009 | Flanagan |
| 7,722,674 B1 | 5/2010 | Grotz |
| 7,749,228 B2 | 7/2010 | Lieberman |
| 7,763,028 B2 | 7/2010 | Lim et al. |

(56) References Cited

U.S. PATENT DOCUMENTS

| | | |
|---|---|---|
| 7,771,463 B2 | 8/2010 | Ton et al. |
| 7,828,849 B2 | 11/2010 | Lim |
| 7,837,734 B2 | 11/2010 | Zucherman et al. |
| 7,846,206 B2 | 12/2010 | Oglaza et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 8,007,498 B2 | 8/2011 | Mische |
| 8,034,110 B2 | 10/2011 | Garner et al. |
| 8,062,375 B2 | 11/2011 | Glerum et al. |
| 8,105,382 B2 | 1/2012 | Olmos et al. |
| 8,142,507 B2 | 3/2012 | McGuckin |
| 8,162,943 B2 | 4/2012 | Justin et al. |
| 8,206,423 B2 | 6/2012 | Siegal |
| 8,246,622 B2 | 8/2012 | Siegal et al. |
| 8,262,737 B2 | 9/2012 | Bagga et al. |
| 8,425,570 B2 | 4/2013 | Reiley |
| 8,465,524 B2 | 6/2013 | Siegal |
| 8,486,149 B2 | 7/2013 | Saidha et al. |
| 8,512,408 B2 | 8/2013 | Miller et al. |
| 8,518,120 B2 | 8/2013 | Glerum et al. |
| 8,535,380 B2 | 9/2013 | Greenhalgh et al. |
| 8,551,171 B2 | 10/2013 | Johnson et al. |
| 8,556,979 B2 | 10/2013 | Glerum et al. |
| 8,579,912 B2 | 11/2013 | Isaza et al. |
| 8,591,582 B2 | 11/2013 | Anderson et al. |
| 8,672,968 B2 | 3/2014 | Stone et al. |
| 8,672,977 B2 | 3/2014 | Siegal et al. |
| 8,679,183 B2 | 3/2014 | Glerum et al. |
| 8,685,098 B2 | 4/2014 | Glerum et al. |
| 8,709,042 B2 | 4/2014 | Greenhalgh et al. |
| 8,777,993 B2 | 7/2014 | Siegal et al. |
| 8,845,731 B2 | 9/2014 | Weiman |
| 8,845,734 B2 | 9/2014 | Weiman |
| 9,050,112 B2 | 6/2015 | Greenhalgh et al. |
| 9,149,286 B1 | 10/2015 | Greenhalgh et al. |
| 9,216,095 B2 | 12/2015 | Glerum et al. |
| 9,259,329 B2 | 2/2016 | Greenhalgh et al. |
| 9,314,349 B2 | 4/2016 | Greenhalgh et al. |
| 9,402,739 B2 | 8/2016 | Weiman et al. |
| 9,408,708 B2 | 8/2016 | Greenhalgh |
| 9,510,885 B2 | 12/2016 | Burger et al. |
| 9,770,339 B2 | 9/2017 | Greenhalgh et al. |
| 10,070,968 B2 | 9/2018 | Greenhalgh et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0038767 A1 | 4/2002 | Trozera |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0171813 A1 | 9/2003 | Kiester |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | Mcguckin |
| 2003/0199981 A1 | 10/2003 | Ferree |
| 2003/0204189 A1 | 10/2003 | Cragg |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | Mckay et al. |
| 2004/0059419 A1 | 3/2004 | Michelson |
| 2004/0059429 A1 | 3/2004 | Amin et al. |
| 2004/0068259 A1 | 4/2004 | Michelson |

(56) References Cited

U.S. PATENT DOCUMENTS

| | | |
|---|---|---|
| 2004/0082954 A1 | 4/2004 | Teitelbaum et al. |
| 2004/0082961 A1 | 4/2004 | Teitelbaum |
| 2004/0087947 A1 | 5/2004 | Lim et al. |
| 2004/0087950 A1 | 5/2004 | Teitelbaum |
| 2004/0092933 A1 | 5/2004 | Shaolian et al. |
| 2004/0092946 A1 | 5/2004 | Bagga et al. |
| 2004/0092988 A1 | 5/2004 | Shaolian et al. |
| 2004/0097927 A1 | 5/2004 | Yeung et al. |
| 2004/0102848 A1 | 5/2004 | Michelson |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2004/0172019 A1 | 9/2004 | Ferree |
| 2005/0010292 A1 | 1/2005 | Carrasco |
| 2005/0015152 A1 | 1/2005 | Sweeney |
| 2005/0022839 A1 | 2/2005 | Savas et al. |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0228472 A1 | 10/2005 | Case et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261695 A1 | 11/2005 | Cragg et al. |
| 2005/0261768 A1 | 11/2005 | Trieu |
| 2005/0261781 A1 | 11/2005 | Sennett et al. |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0022180 A1 | 2/2006 | Selness |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | Mckinley |
| 2006/0058880 A1 | 3/2006 | Wysocki et al. |
| 2006/0079898 A1 | 4/2006 | Ainsworth et al. |
| 2006/0085069 A1 | 4/2006 | Kim |
| 2006/0085070 A1 | 4/2006 | Kim |
| 2006/0089715 A1 | 4/2006 | Truckai et al. |
| 2006/0095123 A1 | 5/2006 | Flanagan |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0142859 A1 | 6/2006 | Mcluen |
| 2006/0149239 A1 | 7/2006 | Winslow et al. |
| 2006/0149349 A1 | 7/2006 | Garbe |
| 2006/0149385 A1 | 7/2006 | Mckay |
| 2006/0155379 A1 | 7/2006 | Heneveld et al. |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0184248 A1 | 8/2006 | Edidin et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0235414 A1 | 10/2006 | Lim et al. |
| 2006/0235423 A1 | 10/2006 | Cantu |
| 2006/0241764 A1 | 10/2006 | Michelson |
| 2006/0253201 A1 | 11/2006 | Mcluen |
| 2006/0264968 A1 | 11/2006 | Frey et al. |
| 2006/0265077 A1 | 11/2006 | Zwirkoski |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055201 A1 | 3/2007 | Seto et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123877 A1 | 5/2007 | Goldin et al. |
| 2007/0123986 A1 | 5/2007 | Schaller |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0219634 A1 | 9/2007 | Greenhalgh et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0276382 A1 | 11/2007 | Mikhail et al. |
| 2007/0282342 A1 | 12/2007 | Niederberger et al. |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0082162 A1 | 4/2008 | Boismier et al. |
| 2008/0124865 A1 | 5/2008 | Lutze et al. |
| 2008/0125864 A1 | 5/2008 | De Villiers et al. |
| 2008/0125865 A1 | 5/2008 | Abdelgany |
| 2008/0133012 A1 | 6/2008 | McGuckin |
| 2008/0140082 A1 | 6/2008 | Erdem et al. |
| 2008/0140179 A1 | 6/2008 | Ladisa |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0208255 A1 | 8/2008 | Siegal |
| 2008/0221687 A1 | 9/2008 | Viker |
| 2008/0243254 A1 | 10/2008 | Butler |
| 2008/0243255 A1 | 10/2008 | Butler et al. |
| 2008/0249625 A1 | 10/2008 | Waugh et al. |
| 2008/0249628 A1 | 10/2008 | Altarac et al. |
| 2008/0281346 A1 | 11/2008 | Greenhalgh et al. |
| 2008/0294205 A1 | 11/2008 | Greenhalgh et al. |
| 2008/0312743 A1 | 12/2008 | Vila et al. |
| 2008/0312744 A1 | 12/2008 | Vresilovic et al. |

(56) References Cited

U.S. PATENT DOCUMENTS

| | | |
|---|---|---|
| 2009/0005871 A1 | 1/2009 | White et al. |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0054991 A1 | 2/2009 | Biyani et al. |
| 2009/0076511 A1 | 3/2009 | Osman |
| 2009/0143859 A1 | 6/2009 | McClellan et al. |
| 2009/0149956 A1 | 6/2009 | Greenhalgh et al. |
| 2009/0163918 A1 | 6/2009 | Levy et al. |
| 2009/0177207 A1 | 7/2009 | Schaller |
| 2009/0182336 A1 | 7/2009 | Brenzel et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2009/0240335 A1 | 9/2009 | Arcenio et al. |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0168862 A1 | 7/2010 | Edie et al. |
| 2010/0191336 A1 | 7/2010 | Greenhalgh |
| 2010/0211176 A1 | 8/2010 | Greenhalgh |
| 2010/0262147 A1 | 10/2010 | Siegal et al. |
| 2010/0292796 A1 | 11/2010 | Greenhalgh et al. |
| 2010/0324560 A1 | 12/2010 | Suda |
| 2011/0009869 A1 | 1/2011 | Marino et al. |
| 2011/0009969 A1 | 1/2011 | Puno |
| 2011/0029083 A1 | 2/2011 | Hynes et al. |
| 2011/0046737 A1 | 2/2011 | Teisen |
| 2011/0054621 A1 | 3/2011 | Lim |
| 2011/0087296 A1 | 4/2011 | Reiley et al. |
| 2011/0106260 A1 | 5/2011 | Laurence et al. |
| 2011/0118785 A1 | 5/2011 | Reiley |
| 2011/0125266 A1 | 5/2011 | Rodgers et al. |
| 2011/0153019 A1 | 6/2011 | Siegal |
| 2011/0166575 A1 | 7/2011 | Assell et al. |
| 2011/0184519 A1 | 7/2011 | Trieu |
| 2011/0230884 A1 | 9/2011 | Mantzaris et al. |
| 2011/0230966 A1 | 9/2011 | Trieu |
| 2011/0257684 A1 | 10/2011 | Sankaran |
| 2011/0282387 A1 | 11/2011 | Suh et al. |
| 2011/0282398 A1 | 11/2011 | Overes et al. |
| 2011/0282453 A1 | 11/2011 | Greenhalgh et al. |
| 2011/0319898 A1 | 12/2011 | O'Neil et al. |
| 2011/0320000 A1 | 12/2011 | O'Neil et al. |
| 2012/0004726 A1 | 1/2012 | Greenhalgh et al. |
| 2012/0004731 A1 | 1/2012 | Viker |
| 2012/0029518 A1 | 2/2012 | Blackwell et al. |
| 2012/0071962 A1 | 3/2012 | Huang et al. |
| 2012/0071980 A1 | 3/2012 | Purcell et al. |
| 2013/0035723 A1 | 2/2013 | Donner |
| 2013/0053852 A1 | 2/2013 | Greenhalgh et al. |
| 2013/0085535 A1 | 4/2013 | Greenhalgh et al. |
| 2013/0138214 A1 | 5/2013 | Greenhalgh et al. |
| 2013/0173004 A1 | 7/2013 | Greenhalgh et al. |
| 2013/0304224 A1 | 11/2013 | Schmidt et al. |
| 2014/0088713 A1 | 3/2014 | Greenhalgh et al. |
| 2014/0155980 A1 | 6/2014 | Turjman et al. |
| 2015/0230931 A1 | 8/2015 | Greenhalgh |
| 2015/0265417 A1 | 9/2015 | Greenhalgh et al. |
| 2015/0351930 A1 | 12/2015 | Greenhalgh et al. |
| 2016/0022429 A1 | 1/2016 | Greenhalgh et al. |
| 2016/0030099 A1 | 2/2016 | Greenhalgh et al. |
| 2016/0058572 A1 | 3/2016 | Greenhalgh et al. |
| 2016/0310291 A1 | 10/2016 | Greenhalgh |
| 2016/0374727 A1 | 12/2016 | Greenhalgh et al. |
| 2017/0119540 A1 | 5/2017 | Greenhalgh |
| 2017/0119541 A1 | 5/2017 | Greenhalgh |
| 2017/0181865 A1 | 6/2017 | Greenhalgh et al. |
| 2017/0196613 A1 | 7/2017 | Greenhalgh et al. |
| 2017/0319353 A1 | 11/2017 | Greenhalgh et al. |
| 2017/0348115 A1 | 12/2017 | Greenhalgh et al. |
| 2018/0256359 A1 | 9/2018 | Greenhalgh |
| 2018/0368986 A1 | 12/2018 | Greenhalgh et al. |

FOREIGN PATENT DOCUMENTS

| | | |
|---|---|---|
| EP | 0758541 | 2/1997 |
| EP | 1804733 | 7/2007 |
| FR | 2874814 | 11/2007 |
| FR | 2900814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| JP | 2012-522961 | 9/2012 |
| SU | 662082 | 5/1979 |
| WO | WO 1988/003781 | 6/1988 |
| WO | WO 1992/014423 | 9/1992 |
| WO | WO 1995/031945 | 11/1995 |
| WO | WO 1996/003092 | 2/1996 |
| WO | WO 1997/000054 | 1/1997 |
| WO | WO 2000/025706 | 5/2000 |
| WO | WO 2000/030523 | 6/2000 |
| WO | WO 2000/044319 | 8/2000 |
| WO | WO 2000/044321 | 8/2000 |
| WO | WO 2001/032099 | 5/2001 |
| WO | WO 2001/078625 | 10/2001 |
| WO | WO 2001/095838 | 12/2001 |
| WO | WO 2002/013700 | 2/2002 |
| WO | WO 2002/032347 | 4/2002 |
| WO | WO 2003/003943 | 1/2003 |
| WO | WO 2003/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/068682 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116760 | 11/2006 |
| WO | WO 2006/116761 | 11/2006 |
| WO | WO 2006/132945 | 12/2006 |
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041665 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/073488 | 6/2007 |
| WO | WO 2007/075411 | 7/2007 |
| WO | WO 2007/076308 | 7/2007 |
| WO | WO 2007/076374 | 7/2007 |
| WO | WO 2007/076376 | 7/2007 |
| WO | WO 2007/076377 | 7/2007 |
| WO | WO 2007/079021 | 7/2007 |
| WO | WO 2007/084239 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/113808 | 10/2007 |
| WO | WO 2007/123920 | 11/2007 |

(56) References Cited

FOREIGN PATENT DOCUMENTS

| WO | WO 2007/124130 | 11/2007 |
|---|---|---|
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/016598 | 2/2008 |
| WO | WO 2008/036505 | 3/2008 |
| WO | WO 2008/070863 | 6/2008 |
| WO | WO 2009/039430 | 3/2009 |
| WO | WO 2009/067568 | 5/2009 |
| WO | WO 2009/114381 | 9/2009 |
| WO | WO 2009/130824 | 10/2009 |
| WO | WO 2010/013188 | 2/2010 |
| WO | WO 2010/121002 | 10/2010 |
| WO | WO 2011/014502 | 2/2011 |
| WO | WO 2011/049949 | 4/2011 |
| WO | WO 2011/142761 | 11/2011 |
| WO | WO 2011/149557 | 12/2011 |
| WO | WO 2012/027490 | 3/2012 |
| WO | WO 2012/040272 | 3/2012 |
| WO | WO 2012/083173 | 6/2012 |
| WO | WO 2013/028808 | 2/2013 |
| WO | WO 2013/119332 | 8/2013 |

OTHER PUBLICATIONS

Database WPI, Week 198004, Thomson Scientific, London, GB; AN 1980-A8866C, XP002690114,-& SU 662 082 A1 (Tartus Univ) May 15, 1979 (May 15, 1979), abstract, figures 1,2.
Franklin, I,J. et al., "Uptake of Tetracycline by Aortic Aneurysm Wall and Its Effect on Inflammation and Proteolysis," *Brit. J. Surger,* 86(6):771-775, Jun. 1999.
Pyo, R. et al., "Targeted Gene Disruption of Matrix Metalloproteinase-9 (Gelatinase B) Suppresses Development of Experimental Abdominal Aortic Aneurysms," *J. Clinical Investigation*,105(11):1641-1649, Jun. 2000.
Tambiah, J. et al., "Provocation of Experimental Aortic Inflammation Mediators and Chlamydia Pneumoniae," *Brit., J. Surgery,* 88(7):935-940, Feb. 2001.
Walton, L.J. et al., "Inhibition of Prostoglandin E2 Synthesis in Abdonminal Aortic Aneurysms," *Circulation,* 48-54, Jul. 6, 1999.
Xu, Q. et al., "Sp1 Increases Expression of Cyclooxygenase-2 in Hypoxic Vascular Endothelium," *J. Biological Chemistry,* 275(32):24583-24589, Aug. 2000.

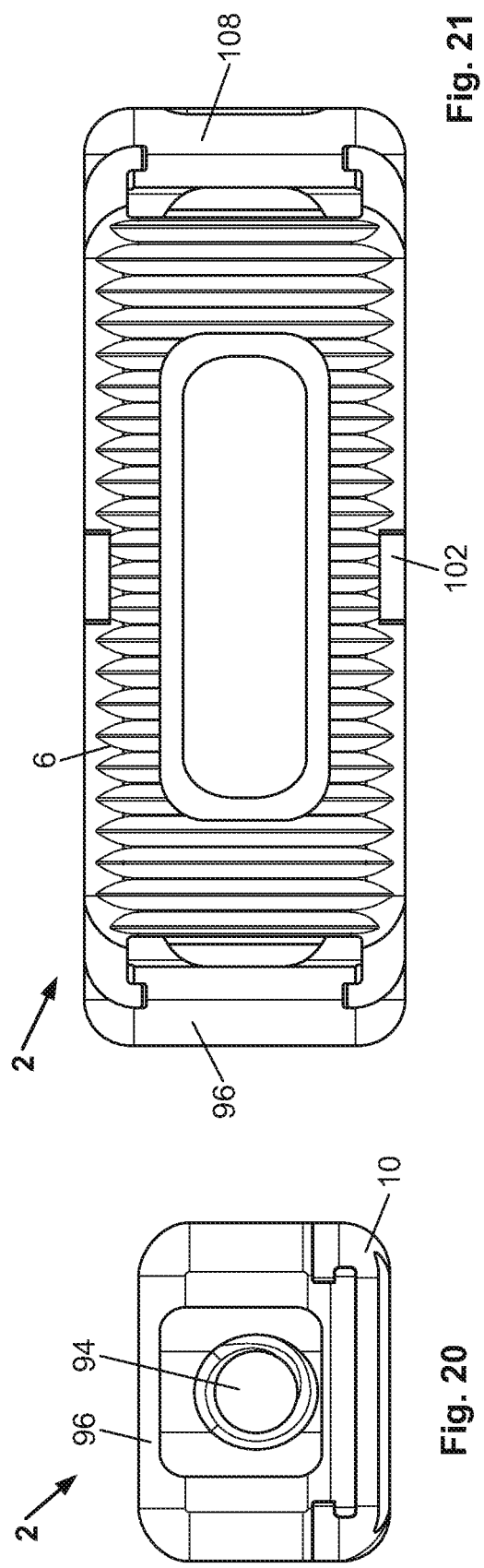

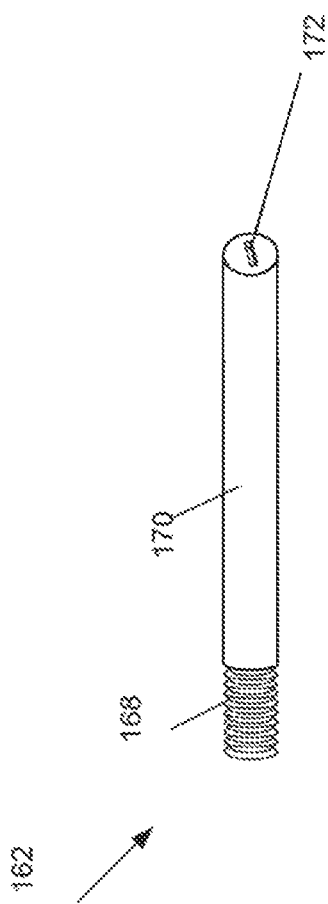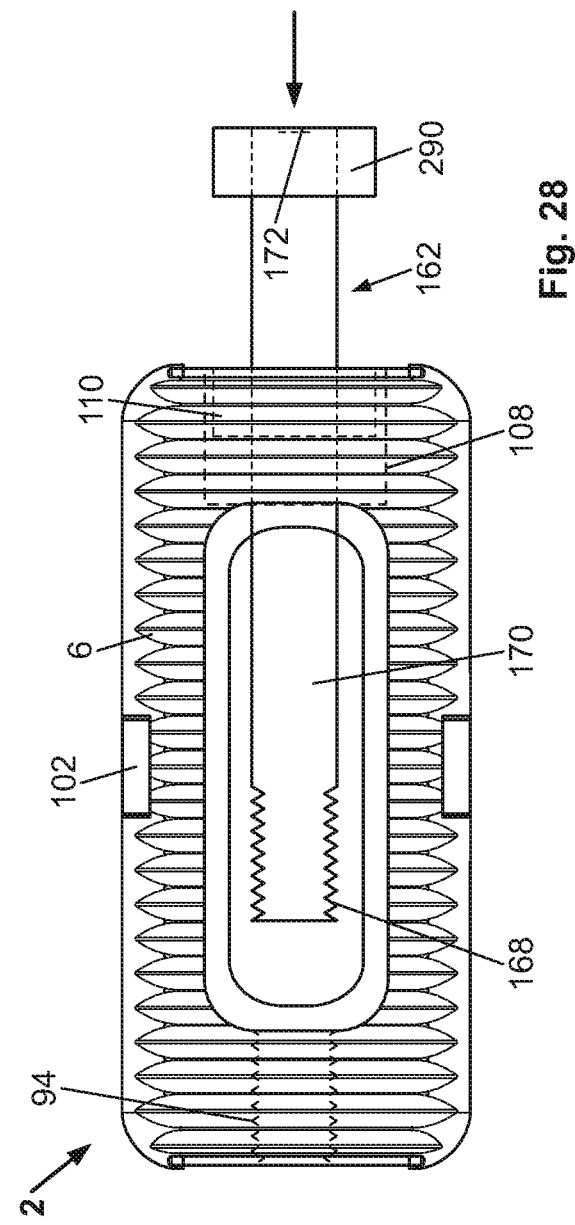

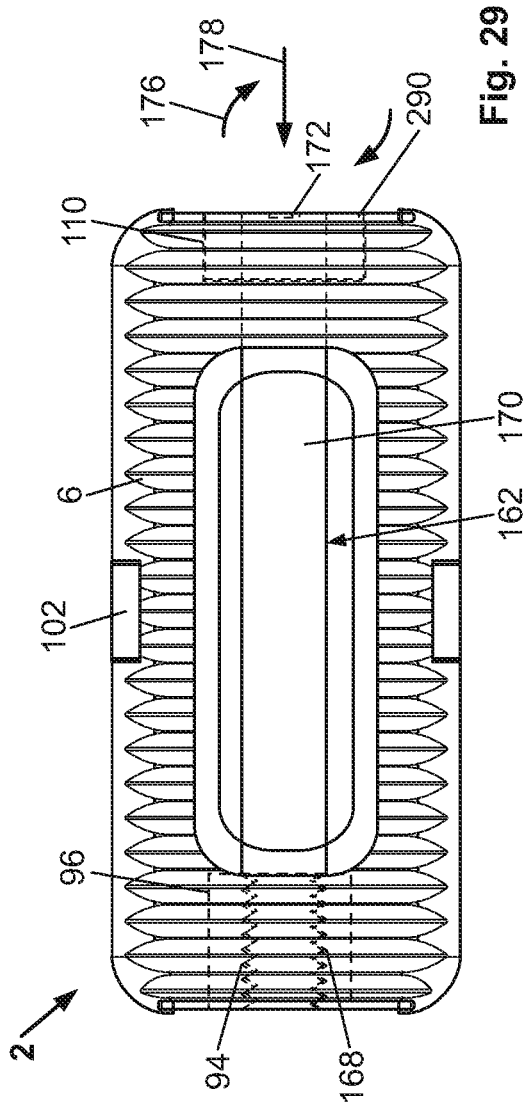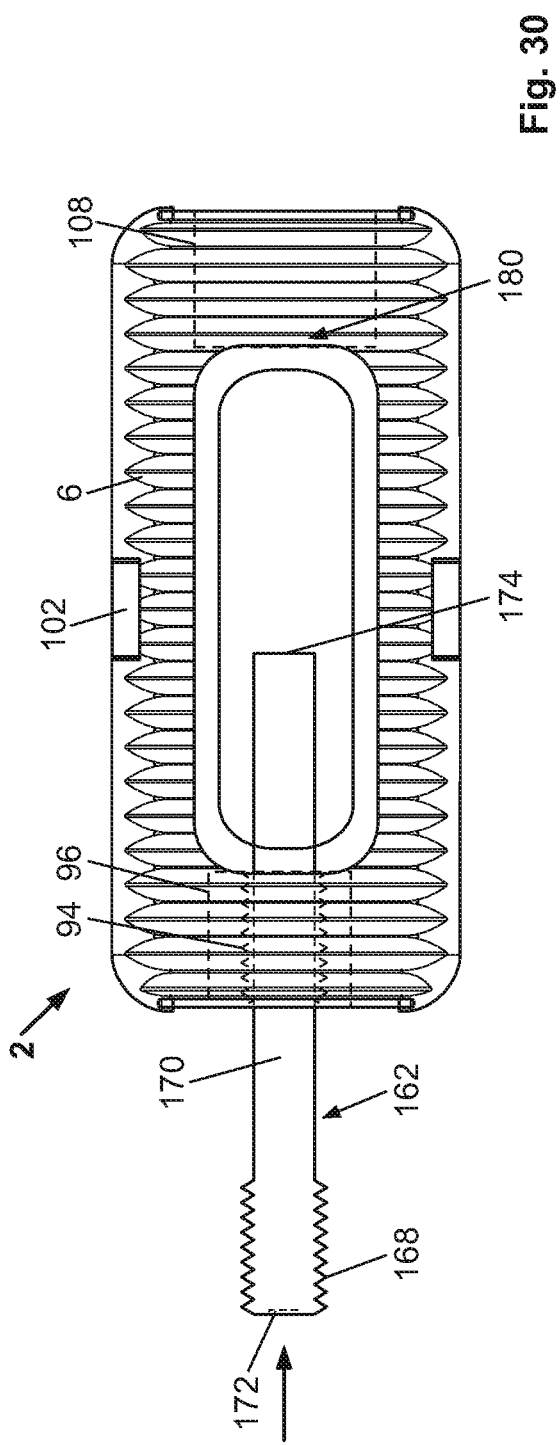

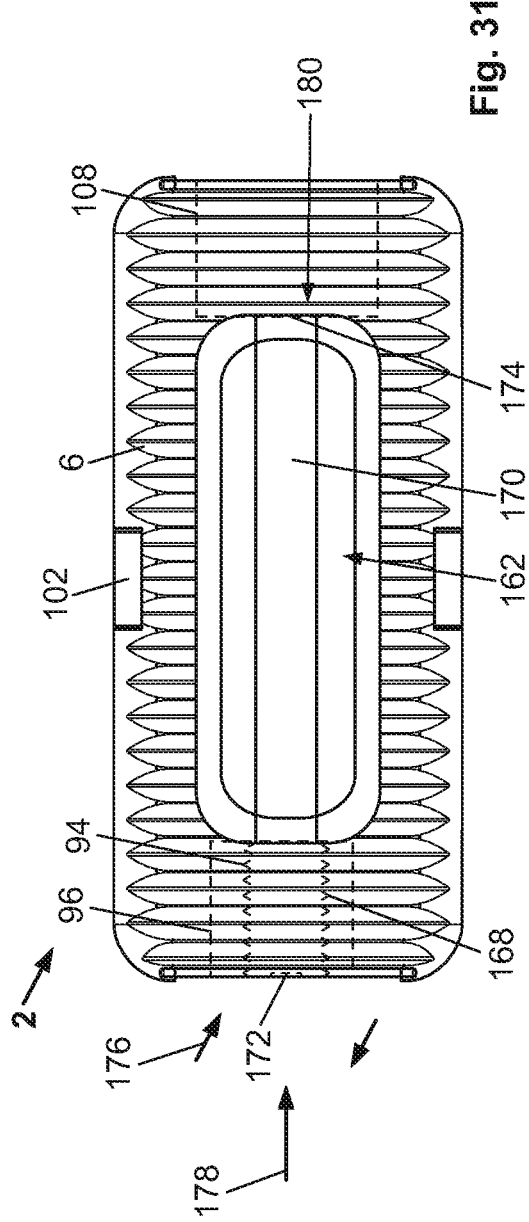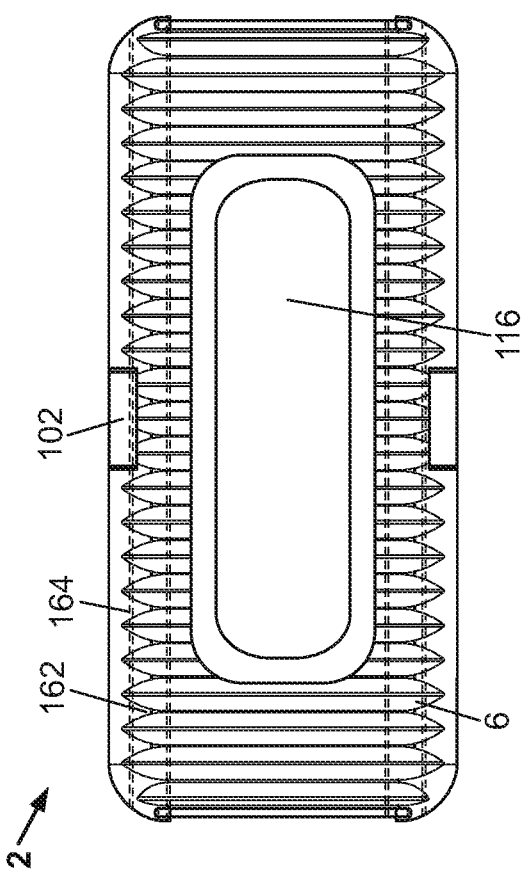

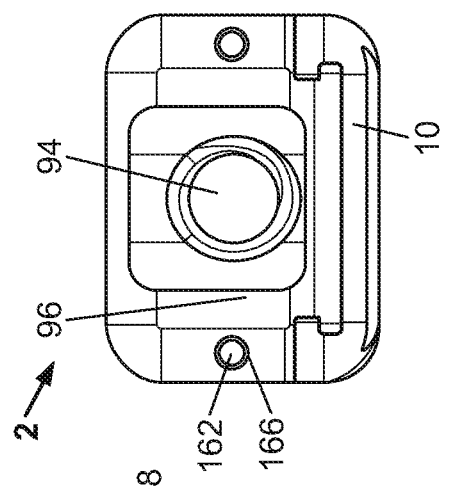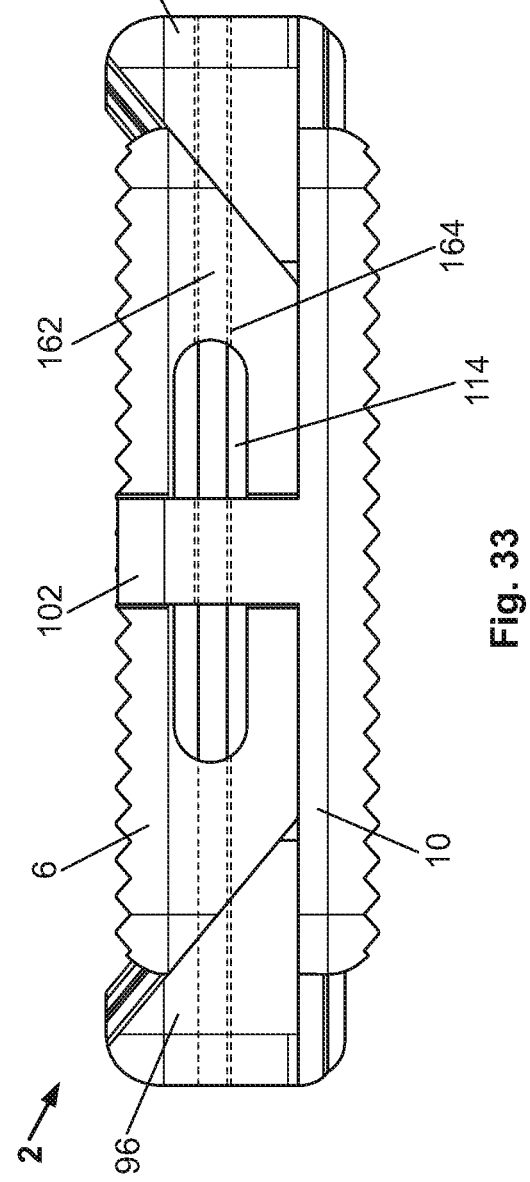

FIXATION DEVICE AND METHOD

CROSS-REFERENCE TO RELATED APPLICATIONS

This application is a continuation of U.S. patent application Ser. No. 14/703,704, filed May 4, 2015, which is a continuation of U.S. patent application Ser. No. 12/693,394, filed. Jan. 25, 2010, now abandoned, which is a continuation-in-part of U.S. patent application Ser. No. 12/617,663, filed Nov. 12, 2009, now issued as U.S. Pat. No. 9,408,708, which claims the benefit of U.S. Provisional Application No. 61/113,691, filed on Nov. 12, 2008, the contents of each of which are incorporated herein by reference in their entireties.

BACKGROUND OF THE INVENTION

1. Technical Field

Devices and methods for fixation of tissue are disclosed. More specifically, the devices and methods can be for inter body vertebral fusion of vertebrae or fusion of other bones to one another.

2. Background of the Art

A vertebroplasty device and method that eliminates or reduces the risks and complexity of the existing art is desired. A vertebroplasty device and method that may reduce or eliminate the need to inject a liquid directly into the compression fracture zone is also desired.

Other ailments of the spine result in degeneration of the spinal disc in the intervertebral space between the vertebral bodies. These include degenerative disc disease and traumatic injuries. In either case, disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, adjacent vertebra can be fixated or fused to each other using devices or bone grafts. These may include, for example, screw and rod systems, interbody spacers (e.g., PEEK spacers or allograft bone grafts) threaded fusion cages and the like.

Some fixation or fusion devices are attached to the vertebra from the posterior side. The device will protrude and result in additional length (i.e., needed to overlap the vertebrae) and additional hardware to separately attach to each vertebrae. Fusion cages and allografts are contained within the intervertebral space, but must be inserted into the intervertebral space in the same dimensions as desired to occupy the intervertebral space. This requires that an opening sufficient to allow the cage or graft must be created through surrounding tissue to permit the cage or graft to be inserted into the intervertebral space.

A spinal fixation or fusion device that can be implanted with or without the need for additional hardware is desired. Also desired is a fixation or fusion device that can be deployed in a configuration where overlapping the fixated or fused vertebrae is not required.

Also desired is an intervertebral device the may be inserted in to the intervertebral space at a first smaller dimension and deployed to a second, larger dimension to occupy the intervertebral space. The ability to insert an intervertebral spacer at a dimension smaller than the deployed dimension would permit less disruption of soft and honey tissue in order to access the intervertebral space.

SUMMARY OF THE INVENTION

A device that can replace or supplement the screw or rod elements of a typical fusion system is disclosed. The device can be placed in the inter-vertebral space to fuse adjacent vertebrae and/or create a bone mass within the inter-vertebral space in a patient's spine.

The device can be less invasive than typical existing devices. For example, the device can be in a compacted (i.e., small) configuration when inserted into a patient and transformed into an expanded (i.e., large) configuration when positioned at the target site. For example, the device can be expanded when the device is between the inferior and superior vertebral body surfaces. The device can create less soft tissue (e.g., bone) disruption than a typical fusion system. The device in an expanded configuration can improve anchoring within the joint, structural stability, and create an environment for bone healing and growth leading to fusion between adjacent vertebrae.

During deployment into tissue (e.g., bone), one, two or more holes can be drilled into the target site to create a deployment hole in which to insert the device. The deployment hole can be round or non-round (e.g., by drilling more than one overlapping or adjacent hole, or crafting a square or rectangular hole), for example to substantially match the transverse cross-section of the device in a contracted configuration.

The device can be cannulated, for example having a lateral (i.e., transverse or latitudinal) and/or lengthwise (i.e., longitudinal) channel through the device. The device can be deployed over a wire or leader, such as a guidewire. The device can be slid over the guidewire, with the guidewire passing through the longitudinal channel of the device.

BRIEF DESCRIPTION OF THE DRAWINGS

FIGS. 17, 18, 20 and 21 are perspective, side, end and top views, respectively, of the variation of the device of FIG. 1 in a pre-deployment configuration.

FIGS. 19 and 22 are side and top views, respectively, of a variation of the device of FIG. 1 in a pre-deployment configuration.

FIG. 22 is illustrated with the top and the base in see-through views for illustrative purposes.

FIGS. 26 and 27 illustrate variations of the locking pin.

FIGS. 28 and 29 illustrate a variation of a method for using the variation of the locking pin of FIG. 26.

FIGS. 30 and 31 illustrate a variation of a method for using the variation of the locking pin of FIG. 27.

FIGS. 32, 33 and 34 are top, side and end views, respectively, of a variation of the device with the locking pin.

DETAILED DESCRIPTION

A device 2 is disclosed that can be inserted into a target site 264 with the device 2 in a compressed or contracted (i.e., small) configuration. Once positioned in the deployment site, the device 2 can be transformed into an expanded (i.e., larger, bigger) configuration. The device 2 can be inserted and expanded in orthopedic target sites 264 for fixation and/or support. For example, the device 2 can be inserted and expanded over a guidewire between adjacent vertebral bodies.

Figure 1:
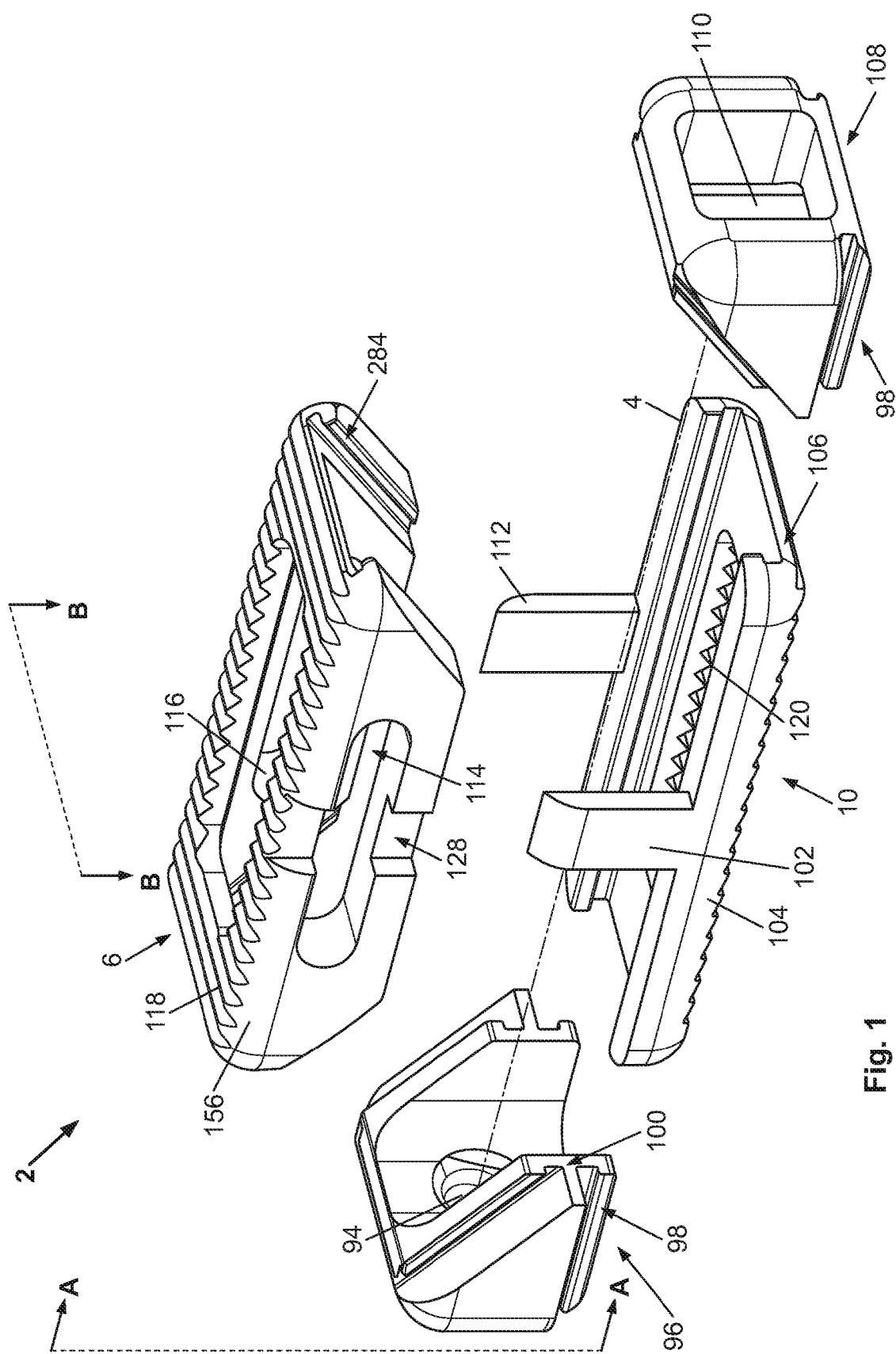
FIG. 1 is an exploded view of a variation of the expandable support device.

FIG. 1 illustrates that the device 2 can have a first longitudinal end and a second longitudinal end along a longitudinal axis 4. The device 2 can have a bottom or plate 286 (bottom and base plate are used interchangeably) and a top plate 6. The base 138 or bottom plate 10 and top plate 6 can be or have plates 286, panels, struts 216 (e.g., legs), ports, cells 88, and combinations thereof. The base plate 10 and top plate 6 can be configured to be slidably attachable to the other. For example, the base (or top) plate can have one or more stability bars 102. The top (or base) plate can have one or more stability grooves 128. The stability bars 102 can be configured to be slidably attachable to the stability grooves 128.

The slidable attachment of the top and base plates can permit the base 138 to move radially (with respect to the longitudinal axis 4) relative to the top and vice versa.

The top plate 6 can have a high-friction and/or low-friction texture extending radially away from the base 138. For example, the top plate 6 can have one or numerous rows of top teeth 118. The bottom plate 10 can have a high-friction and/or low-friction texture extending radially away from the base plate. For example, the bottom plate 10 can have one or numerous rows of bottom teeth 104. The top teeth 118 and the bottom teeth 104

The top plate 6 can have one or more side ports 114 and/or top ports. The base plate can have one or more base ports 120 and/or side ports 114. The base ports 120, side ports 114, and/or top ports can be ingrowth channels 28. The ports can be circular, square, triangular, oval, elongated in the longitudinal direction, elongated in the radial direction, or combinations thereof.

The top plate 6 can have a top chamfer 156. The base plate can have a base chamfer, The chamfers can be atraumatic edges. The chamfers can extend along the perimeter of the base 138 and/or top.

The device 2 can have one, two or more wedges 18, for example a first side ramp 96 on a first longitudinal side of the base plate and a second side ramp 108 on a second longitudinal side of the base plate. The side ramps can be configured to be slidably attachable to the base plate.

The ramps 22 and top plate 6 can be brought within proximity of the base plate. The ramps 22 can be slidably attached to the base plate. The ramps 22 can have ramp second tongues and grooves 98. The base plate can have one or more base tongues and grooves 106. The ramp second tongues and grooves 98 can be configured to slidably attach to the base tongues and grooves 106.

The ramps 22 can be configured to be slidably attachable to the top plate 6. For example, the ramps 22 can have ramp first tongues and grooves 100. The top plate 6 can have top tongues and grooves 284. The ramp first tongues and grooves 100 can slidably engage the top tongues and grooves 284.

The first tongues and grooves can be at a ramp angle 136 with respect to the second tongues and grooves. The ramp angle 136 can be from about 15° to about 75°, more narrowly from about 30° to about 60°, for example about 45°.

One or more of the ramps 22 can have a ramp locking plate port 110. The ramp locking plate ports 110 can each be configured to receive a ramp locking plate. The ramps 22 can each have ramp ports, such as the threaded ramp ports. The threaded ramp ports can pass through the ramps 22, for example opening into the ramp locking plate port 110.

Figure 2:
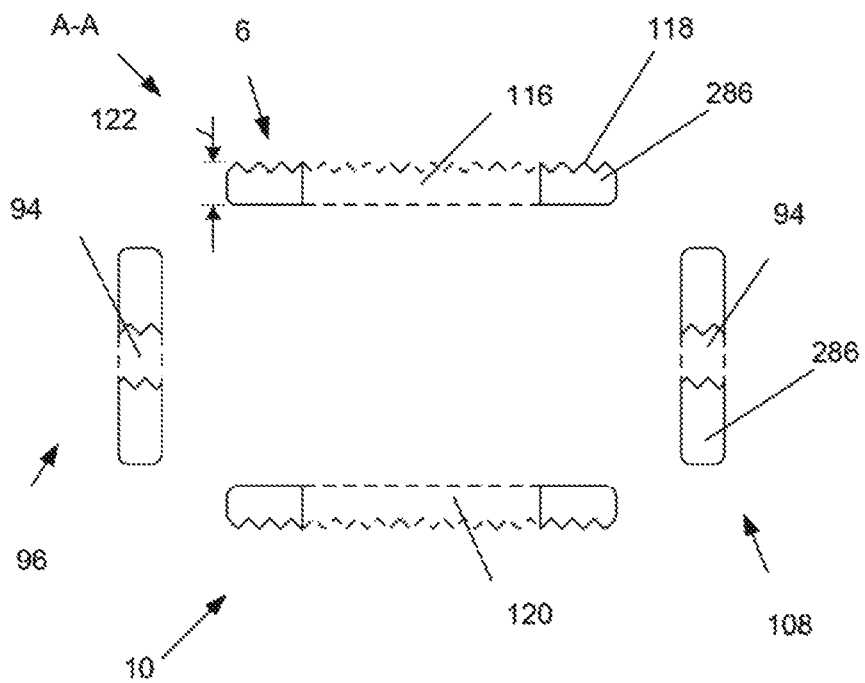
FIGS. 2 through 4 illustrate variations of cross-section A-A of FIG. 1.

FIG. 2 illustrates that each of the top, or base 138 or bottom plates can have a plate thickness 122. The plates 286 can be thinned adjacent to some or all ports. The plate thickness 122 can be substantially constant along the length of the top or base 138. The plate thickness 122 can be non-constant, for example along the length and/or width of the top port or base port 120 and the top teeth 118 or base teeth. Each plate 286 of the first side ramp 96 and the second side ramp 108 can have a substantially constant plate thickness 122 along the height of the plate 286 save for the respective ramp ports.

Figure 3:
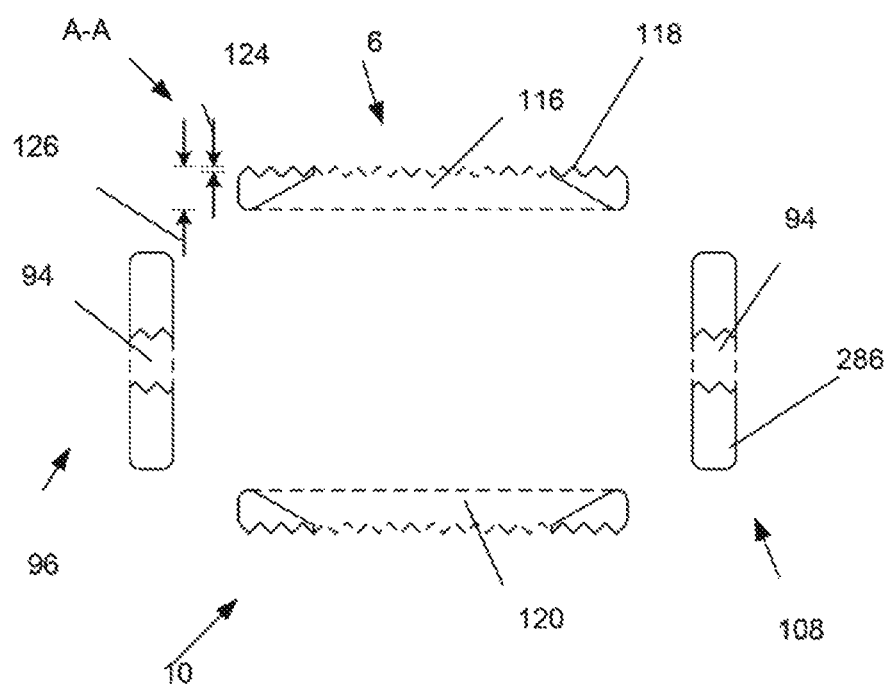

FIG. 3 illustrates that the top and/or bottom plates can thin as the plate 286 nears the port. For example, the plate 286 can have a maximum plate thickness 126 and a minimum plate thickness 124. The maximum plate thickness 126 and minimum plate thickness 124 can be measured with or without accounting for the change in thickness due to the teeth. The minimum plate thickness 124 can be substantially less than the maximum thickness 126. The minimum plate thickness 124 can be substantially 0. The plate 286 can slope outward (as shown), inward, or a combination of both (e.g., sloping inward and outward concurrently to form the rim of the port at a radius from the longitudinal axis between the radii of the outer and inner surfaces of the plate 286).

When the device 2 is in a deployed configuration in vivo, the device 2 can be partially or substantially filled with a liquid, gel, or solid (e.g., in small parts or granules) filler 262 material, or combinations thereof, such as bone morphogenic powder or any other material disclosed herein or combinations thereof. The filler 262 material can contact or be in near contact with the surrounding tissue near the edge of the ports, for example where the plate 286 is thinned. The filler 262 can be inserted into the device 2 before, and/or during (i.e., prepacked), and/or after the device 2 is inserted and/or expanded in the target site.

As the device 2 is expanded and contracted, the volume of the interior channel of the device (i.e., defined between the top and base plates and the opposing ramps) can remain constant. For example, filler can be inserted into the device 2 before the device is radially expanded. The device 2 can be longitudinally contracted and radially expanded (e.g., expanded in height). The ratio of the volume of filler to the volume of the interior channel of the device can then remain substantially constant as the device is radially expanded. For example, the decrease in volume of the interior channel of the device caused by the contracting ramps can be substantially equivalent to the increase in volume of the interior channel of the device 2 caused by the radially expanding top and base plates.

Figure 4:
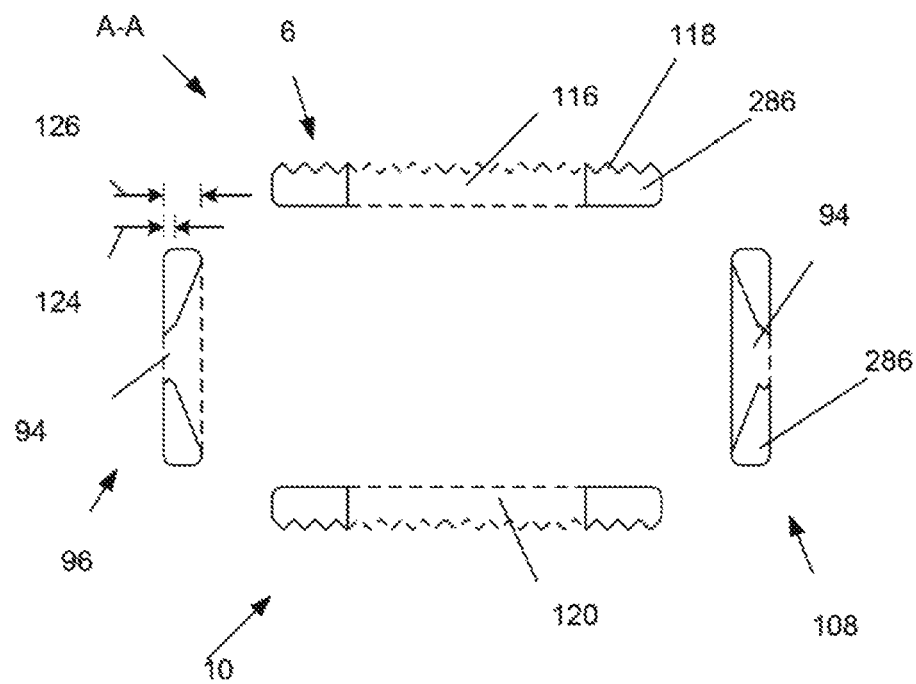

FIG. 4 illustrates that the plates 286 of the first side ramp 96 and/or the second side ramp 108 can thin as the plate 286 nears the threaded ramp port(s). The minimum plate thickness 124 can be substantially less than the maximum plate thickness 126. The minimum plate thickness 124 can be substantially 0. The plate 286 can slope outward (as shown), inward, or a combination of both (e.g., sloping inward and outward concurrently to form the rim of the port at a radius from the longitudinal axis between the radii of the outer and inner surfaces of the plate 286).

Figure 5:
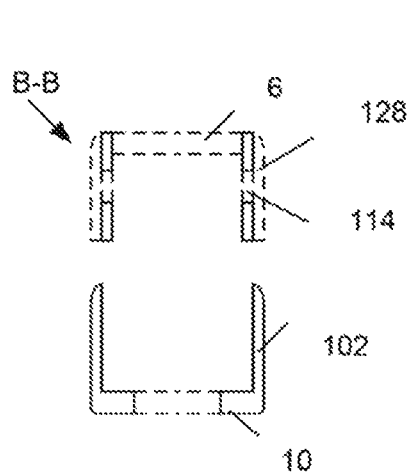
FIGS. 5 and 6 illustrate variations of cross-section B-B of FIG. 1.

FIG. 5 illustrates that the stability bars 102 can be configured to slide into the stability groove 128 when the top and base plates intersect. The radially inner surface of the stability bar 102 can be substantially the same or a greater radius from the longitudinal axis of the expandable support device 188 as the radius of the radially outer surface of the top plate 6 adjacent to the side port 114 (i.e., within the stability groove 128). The stability bar 102 can be configured to not directly attach to the top plate 6 when the top is translated into the base plate, or the stability bars 102 can be configured to bias inward against and frictionally hold the top when the top plate 6 is translated into the base plate.

Figure 6:
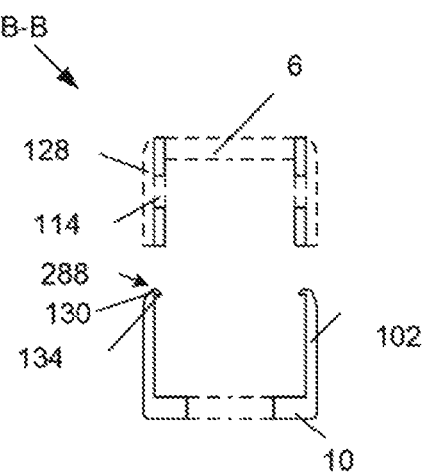

FIG. 6 illustrates that the stability bars 102 can have one or more latches 130 along the length of the stability bar 102, for example at the terminal end of the stability bars 102, as shown. The latch 130 can be configured to attach to the top plate 6. The latch 130 can protrude radially inward. The latch 130 can have a latch top 288 and a latch bottom 134.

The latch top 288 can be configured to allow the top to pass over the latch 130. For example, the latch top 288 can be rounded and configured to push radially outward and clear of the top plate 6 when the top is pressed down into the latch top 288. The latch bottom 134 can be configured to grasp or otherwise attach to the top when the top is translated to a particular location into the base plate.

The stability bars 102 can be configured to resiliently bend radially outward and/or inward.

Figure 7:
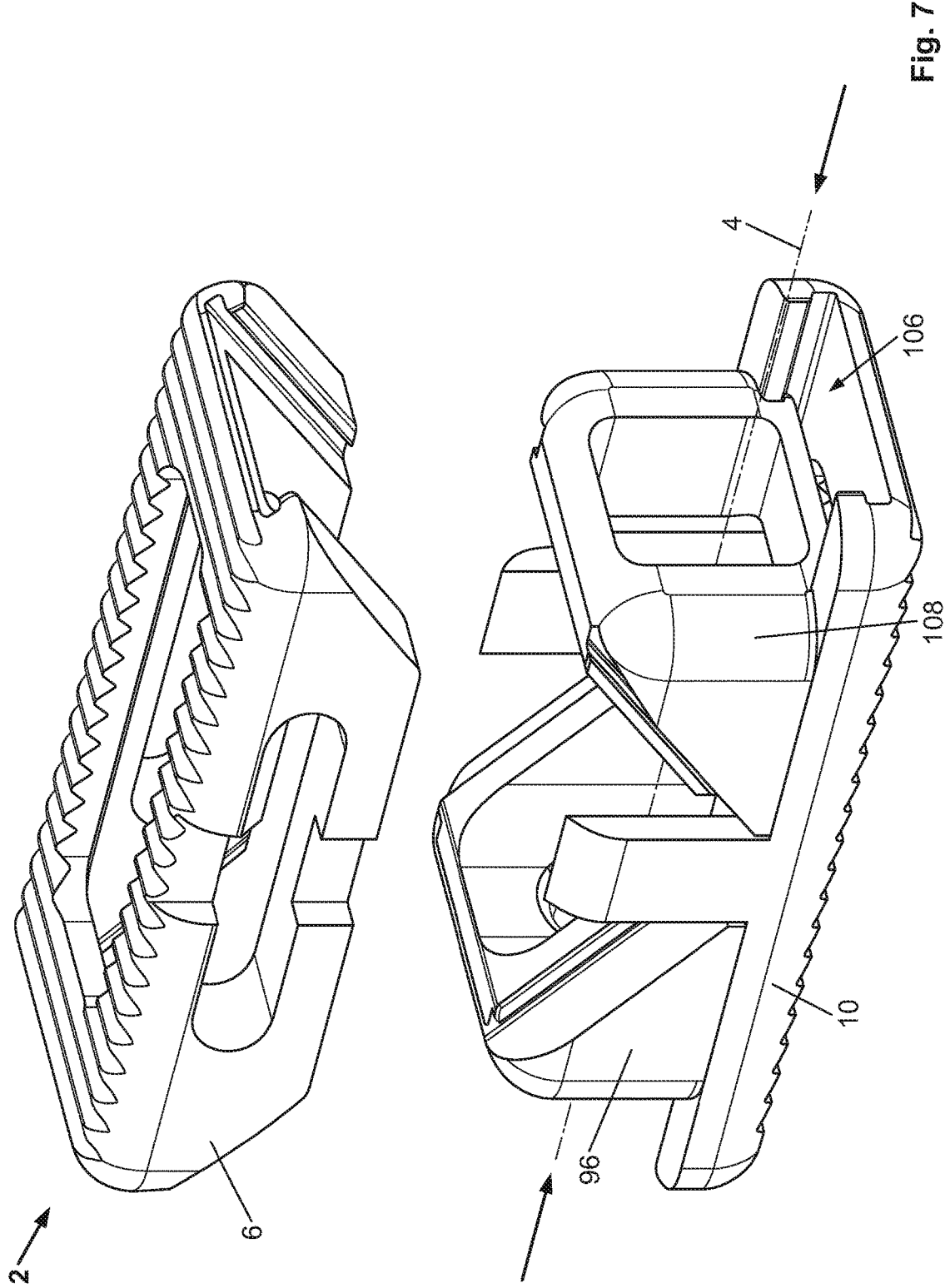
FIG. 7 illustrates the variation of the expandable support device of FIG. 1 with the ramps slidably attached to the base.

FIG. 7 illustrates that the ramps 22 can be slidably attached, as shown by arrows, to the base plate before the ramps 22 are slidably attached to the top plate 6. The ramp second tongues and grooves 98 can be slidably engaged with the base tongues and grooves 106, as shown in FIGS. 12, 13 and 14.

Figure 8:
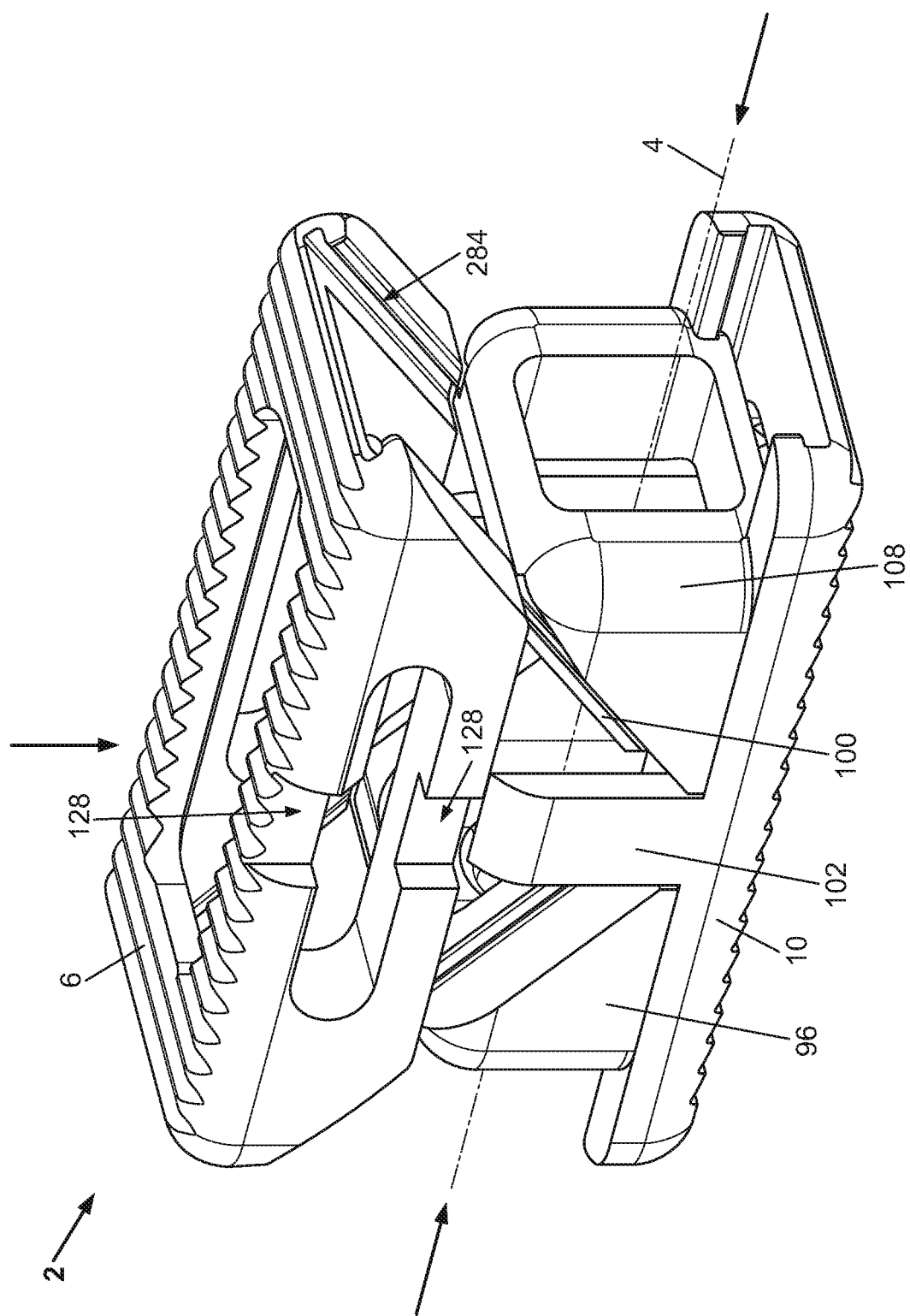
FIGS. 8 and 9 are perspective and side views, respectively, of the variation of the expandable support device of FIG. 7 with the top and ramps in pre-assembly positions.
Figure 9:
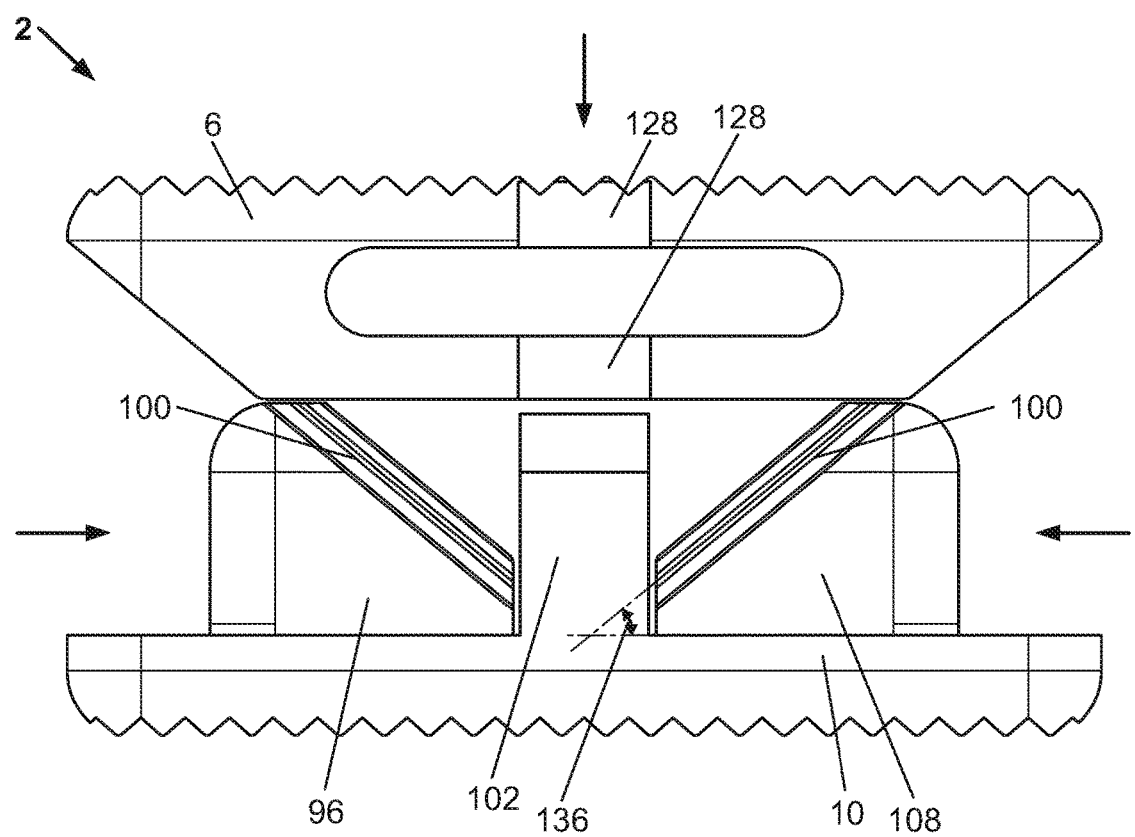

FIGS. 8 and 9 illustrate that the ramps 22 can be positioned, as shown by arrows, so that one or both ramp first tongues and grooves 100 can be aligned to slidably engage the top tongues and grooves 284 as the top plate 6 is translated toward the base plate, as shown by arrows. The stability bar 102 can be slid into the stability groove 128.

Figure 11:
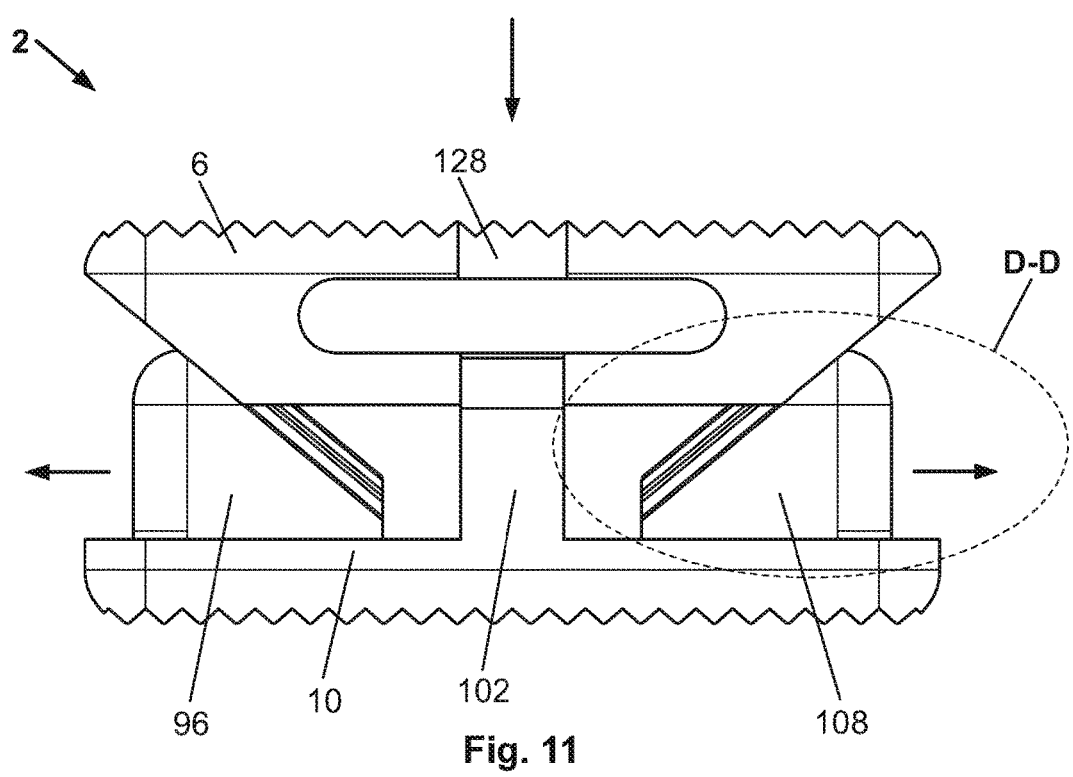
FIGS. 10, 11 and 12 are perspective, side and end views, respectively of the variation of the device of FIG. 1 in an assembled configuration.
Figure 10:
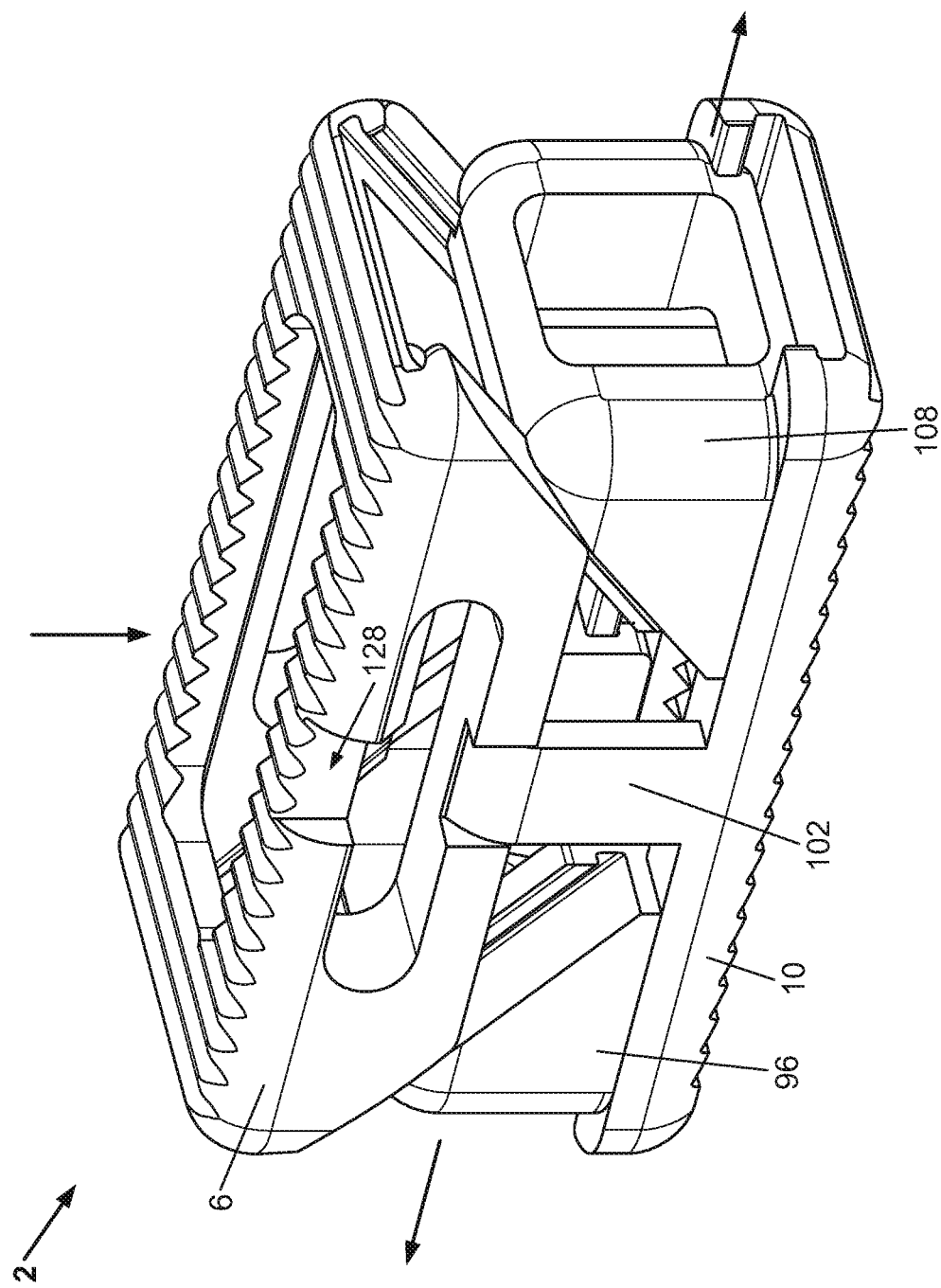
Figure 12:
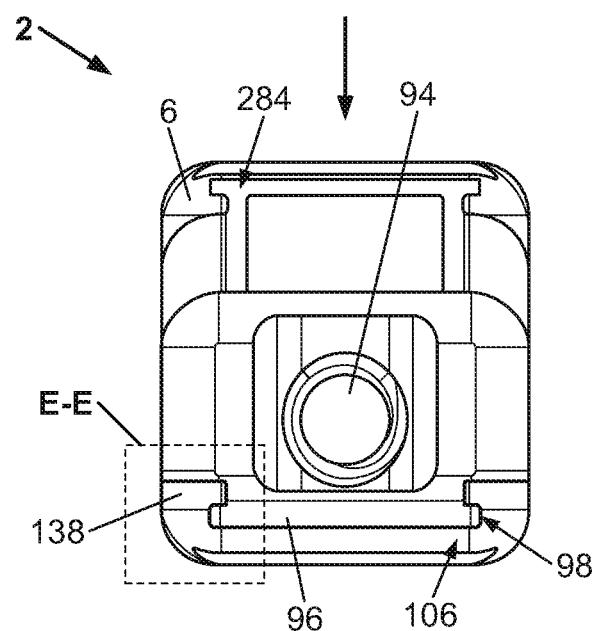

FIGS. 10 through 12 illustrate that as the top plate 6 is translated toward the base plate, as shown by arrows, the top plate 6 can slidably engage one or more of the ramps 22. The first tongues and grooves can slidably engage the top tongues and grooves 284.

Figure 13:
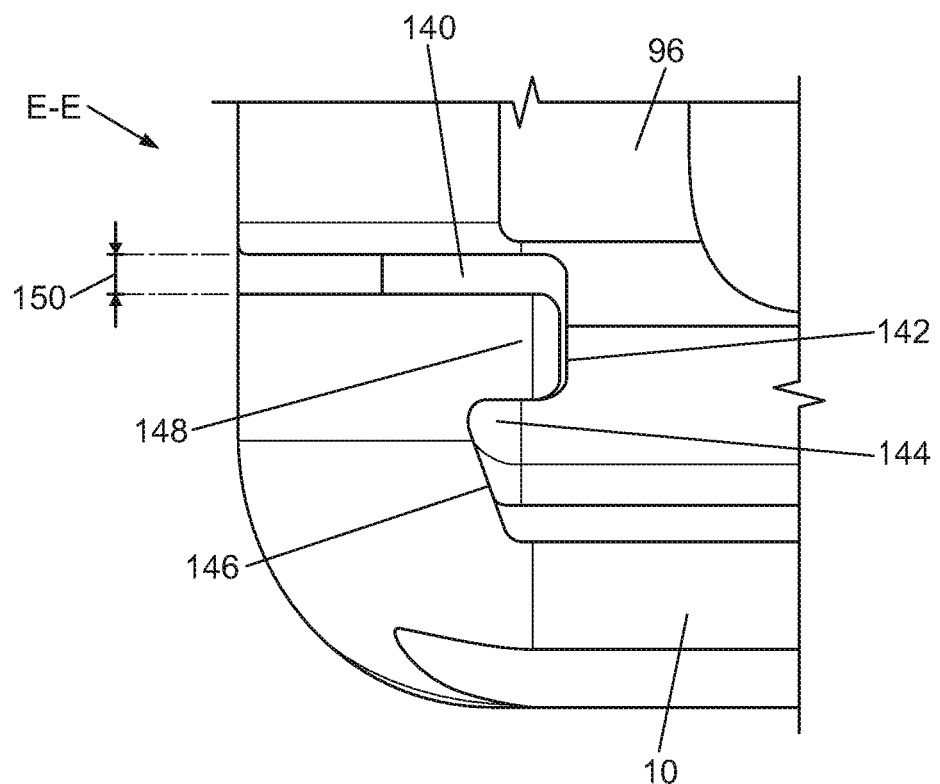
FIG. 13 is a variation of close-up section E-E of FIG. 12 in a first configuration.
Figure 14:
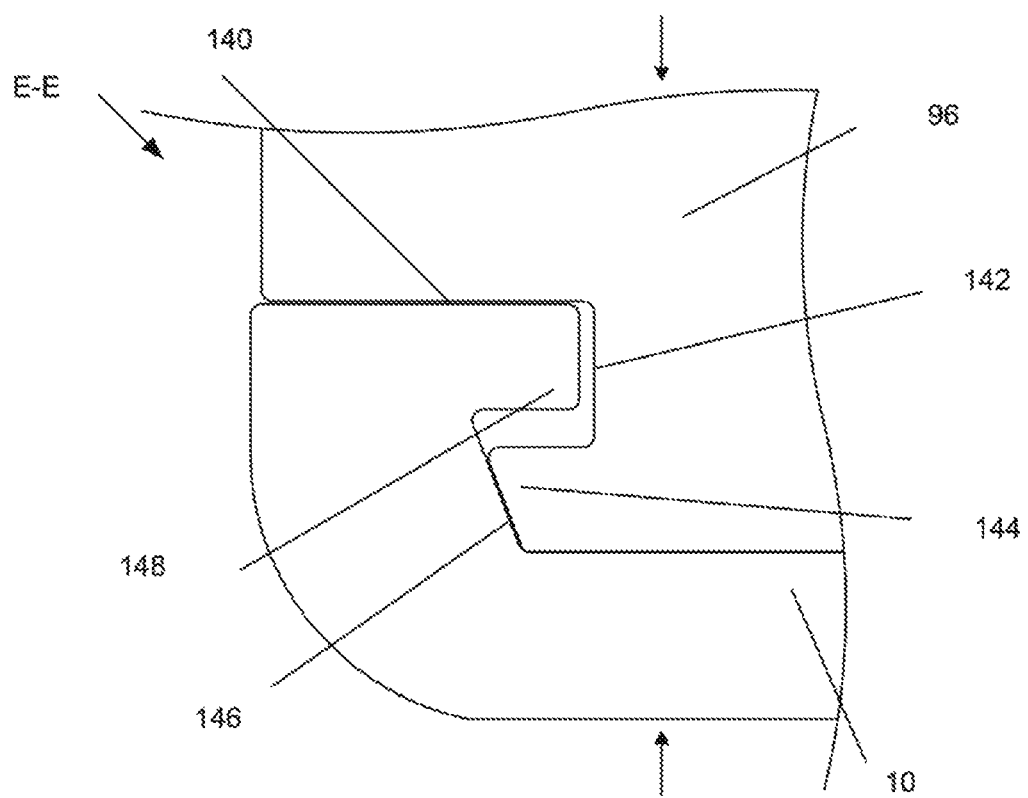
FIG. 14 is a variation of close-up section E-E of FIG. 12 in a second configuration.

FIG. 13 illustrates that there can be a substantial ramp gap 140 between the side ramp and the base plate, for example before the expandable support device 188 is completely deployed. The ramp gap 140 can have a ramp gap height 150. The ramp gap height 150 can vary, for example, from about 0 mm (0 in.) to about 4 mm (0.2 in.). The side ramps can substantially slide along the base plate. For example, the ramp second tongue and groove 98 can slide along the base tongue and groove 106, separated by the ramp gap 140. Most or all of the friction in this configuration can be created by the ramp second tongue in contact with the base tongue 148 and/or side of the base groove 146.

The wall of the base groove 146 can have an outwardly slanted configuration relative to the height of the wall of the base groove 146 from the bottom of the base plate.

FIG. 14 illustrates that the first side ramp 96 and the base 138 can be pressed into or otherwise translated toward each other. For example, after implantation of the device 2, the surrounding tissue in the in vivo environment can naturally compress the device 2.

The ramp gap 140 can be substantially closed. The ramp gap height 150 can be substantially about 0. The side ramps can be substantially friction fit along the base plate. For example, the friction in this configuration can be created along the top surface of substantially the entire base plate including the top of the base tongue 148, and the bottom surface of substantially the entire side ramps.

As the side ramp is pushed, as shown by arrows, toward the base plate, the ramp second tongues 144 can be pressed between the base grooves 146, for example, frictionally fitting the side ramps into the base plate. The base grooves 146 can be tapered, as shown, to force the ramp second tongues 144 to wedge fit or press fit into the base grooves 146 when the side ramp is pushed towards the base plate.

The side ramps can have less friction with the base plate in the configuration of the expandable support device 188 of FIG. 13 than in the configuration of the expandable support device 188 of FIG. 14.

Figure 15:
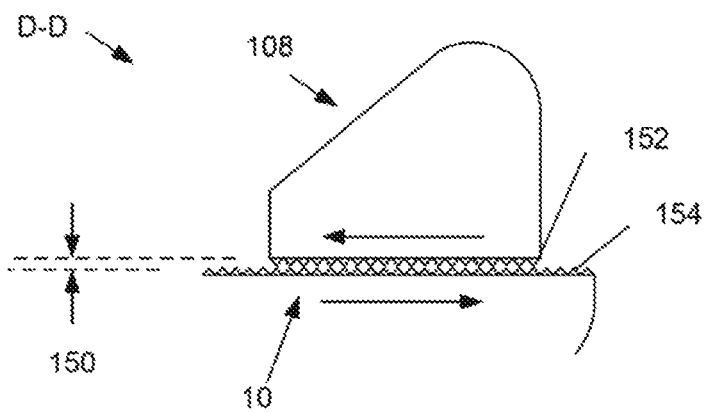
FIGS. 15 and 16 are a variation close-up section D-D of FIG. 11 in first and second configurations, respectively.

FIG. 15 illustrates that the second side ramp 108 (and/or the first side ramp 96, not shown) can have ramp bottom teeth 152 on the side of the second side ramp 108 (and/or first side ramp 96) facing the base plate. The ramp bottom teeth 152 can extend into the ramp gap 140. Either or both side ramps can have teeth on any and/or all sides of the side ramp, for example the surfaces that contact the base plate and the top plate 6. The top plate 6 can have additional teeth, not shown, along surfaces that contact the side ramps.

The ramp bottom teeth 152 and/or base interior teeth 154 can be unidirectionally or bidirectionally oriented (i.e., providing additional resistance against movement in one direction, or substantially the same resistance against movement in either direction).

As the side ramp translates, as shown by arrows, with respect to the base plate, the ramp gap height 150 is substantially non-zero, as shown in FIGS. 13 and 15. When the ramp gap height 150 is substantially non-zero, the ramp bottom teeth 152 can slide over the base interior teeth 154.

Figure 16:
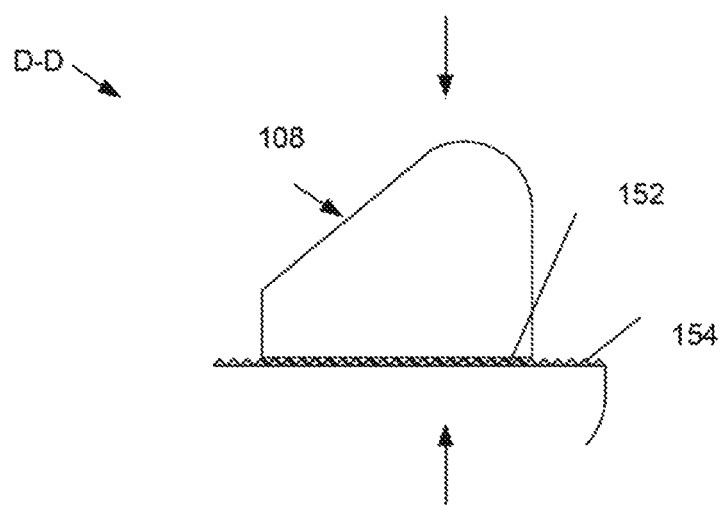

FIG. 16 illustrates that when the side ramp and base plate are pressed together, as shown by arrows, for example when deployed in vivo, the ramp gap height 150 can be minimized, for example approaching about 0 mm (0 in.). The ramp bottom teeth 152 can interlock with the base interior teeth 154. The interlocked ramp bottom teeth 152 and base interior teeth 154 can provide an interference fit or otherwise prevent or minimize the side ramp translating relative to the base plate.

In place of, or in addition to, the ramp bottom teeth 152 and/or the base top teeth, the respective surfaces can have high friction surfaces, for example a textured (e.g., knurled) surface and/or coated with a high friction material. The respective surfaces can also be smooth, having no teeth or texturing.

The side ramp can be pulled away from the base plate by reducing the compressive force between the side ramp and the base plate and pulling or pushing the side ramp.

The side ramp can have a belt and suspenders lock with the base plate.

Figure 17:
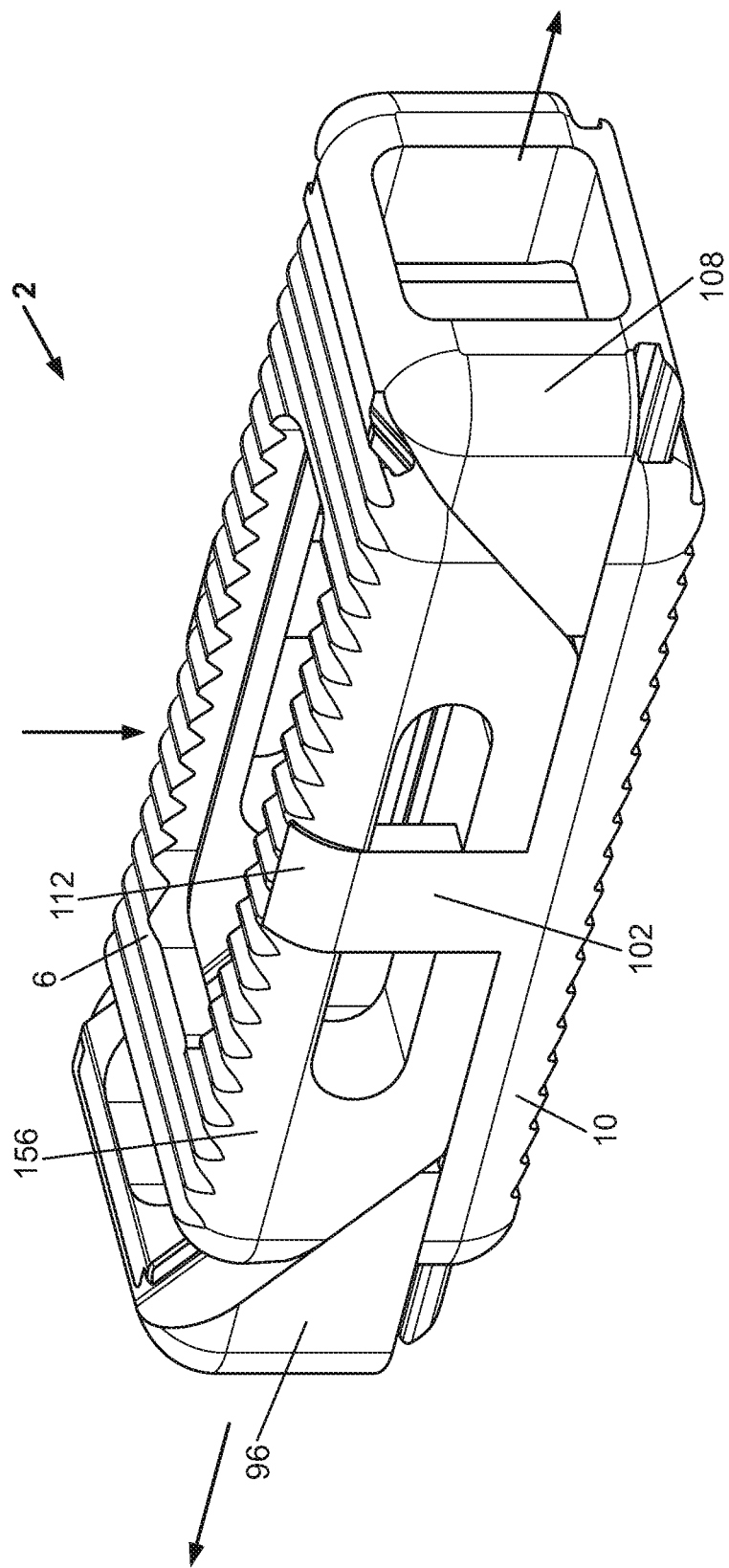
Figure 18:
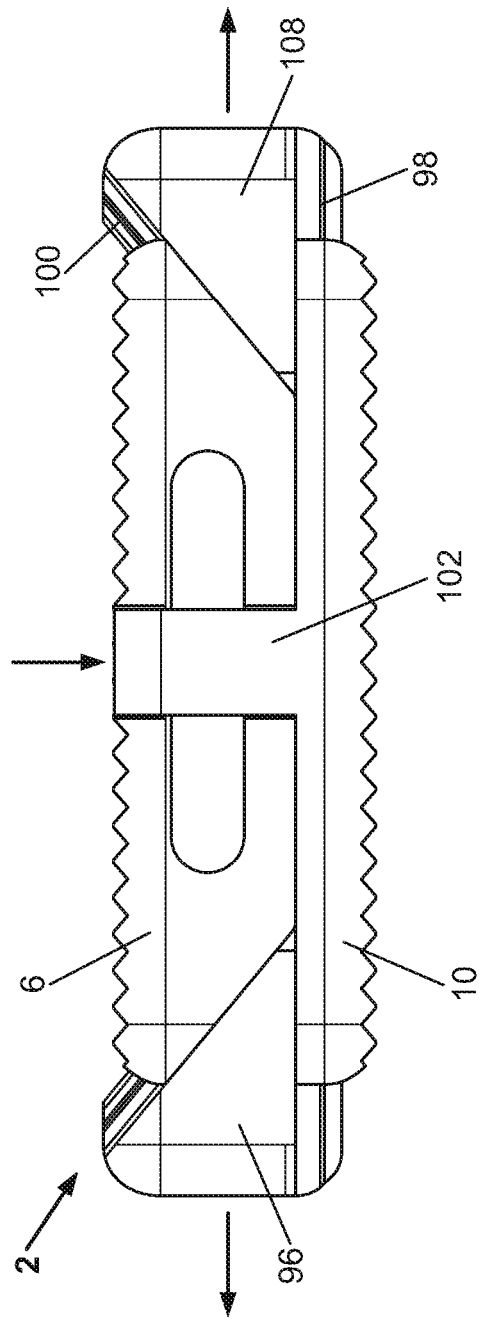

FIGS. 17, 18, and 20 illustrate that the ramps can be pushed outward, as shown by arrows, toward each ramp's respective longitudinal side of the base plate. The ramps 22 can be pushed outward, for example, by a deployment or other tool. When the ramps 22 are slid outward, as shown, the top plate 6 and base plate can translate toward each other, as shown by arrow. The top plate 6 and base plate can then have a radially compressed (e.g., only in the "y"-axis or from the top of the page to the bottom of the page of FIGS. 17, 18, and 20) configuration. The top plate 6 can interference fit against the bottom plate 10 when the expandable support device 188 is fully radially compressed, as shown. The interference fit of the top against the bottom plate, and the slidable attachment of the ramps 22 to the top and the bottom plate 10 can lock the top plate 6, base plate and ramps 22 together (e.g., not allowing any to separate). The device 2 can be attached to a deployment tool 80 (e.g., by removably attaching to one or more ramp ports) and/or delivered to a target site 264 in the radially compressed configuration.

Figure 19:
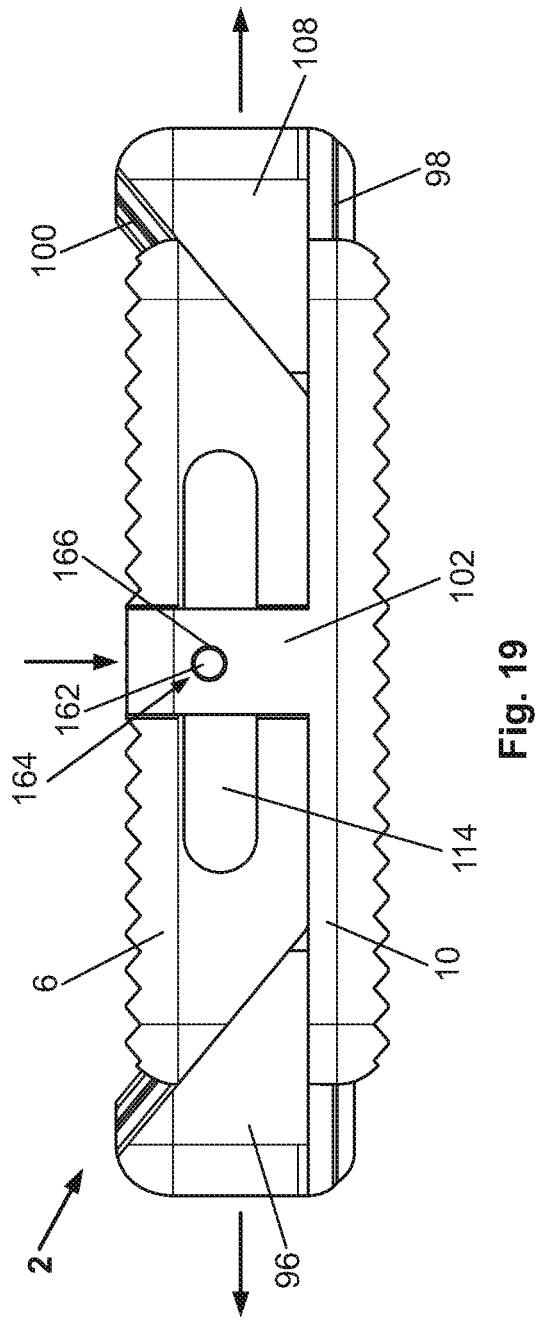

FIGS. 19 and 22 illustrate that one or more locking pin channels 164 can be defined transversely through the device 2. A locking pin 162 can be inserted through each locking pin channel 164. The locking pin 162 can be inserted through the locking pin channel 164 after the device 2 has been inserted at the target site 264 and expanded. The locking pin channel 164 can be defined by locking pin ports 166 on the stability bars 102 and the side port 114. The locking pin ports 166 can be circular, as shown, oval, or combinations thereof.

The locking pin 162 can he configured to limit the vertical expansion of the device 2. For example, the locking pin 162 can be configured to substantially prevent the device 2 from disassembling.

Figure 23:
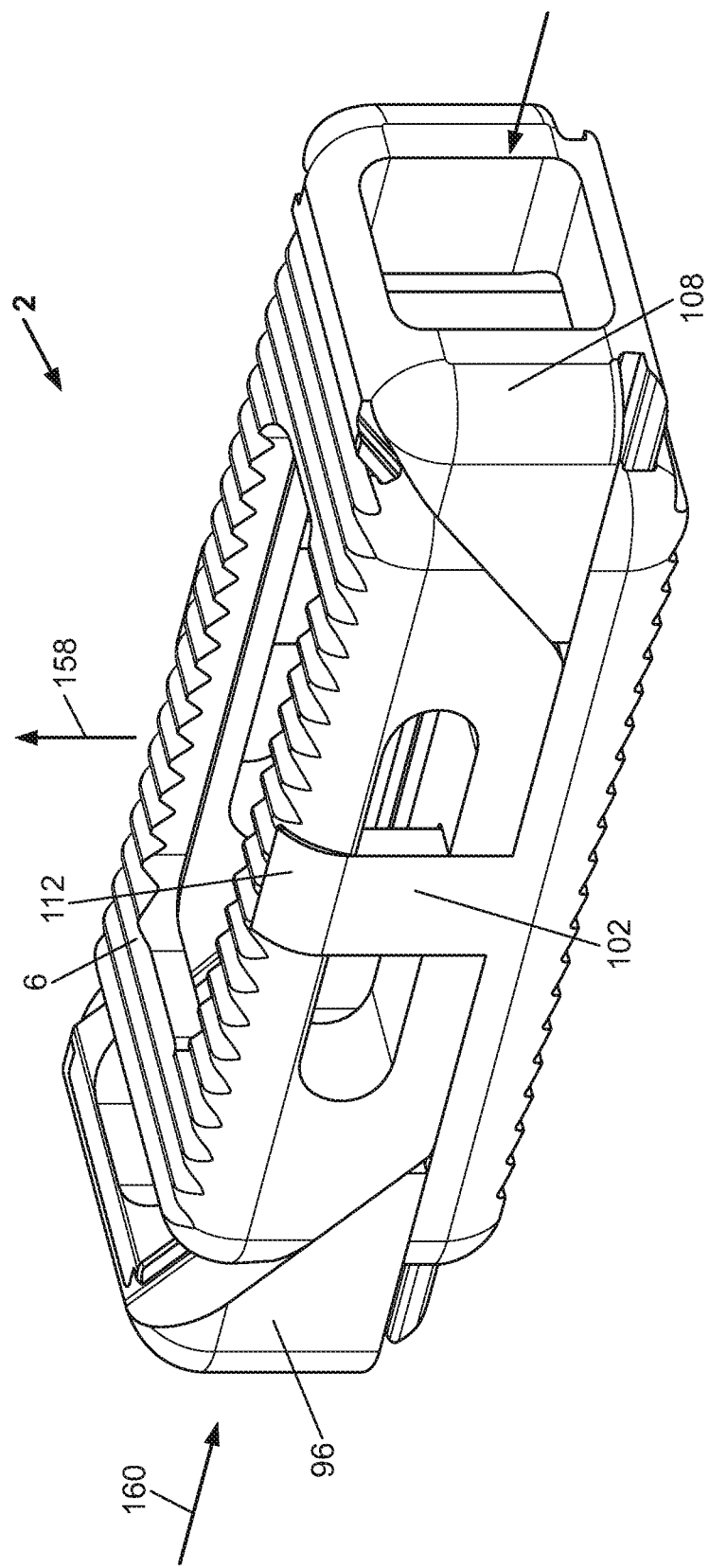
FIG. 23 illustrates a method of longitudinally compression and radially expanding the variation of the device of FIG. 17, for example after deployment at a target site.

FIG. 23 illustrates that the device 2 can be longitudinally compressed, as shown by arrows, resulting in radial and/or vertical expansion, as shown by arrow, for example performed after the device 2 is positioned within a vertebra or between vertebrae. The ramps 22 can be slidably translated along the longitudinal axis and inward and/or toward the center of the device 2. The expansion 92 of the device 2 can increase the height and provide structure support for a compressed or otherwise damaged vertebra (e.g., when the device 2 is deployed within a vertebra) and/or return adjacent vertebrae to a more natural/physiological configuration (e.g., when the device 2 is deployed between adjacent vertebrae).

Figure 24:
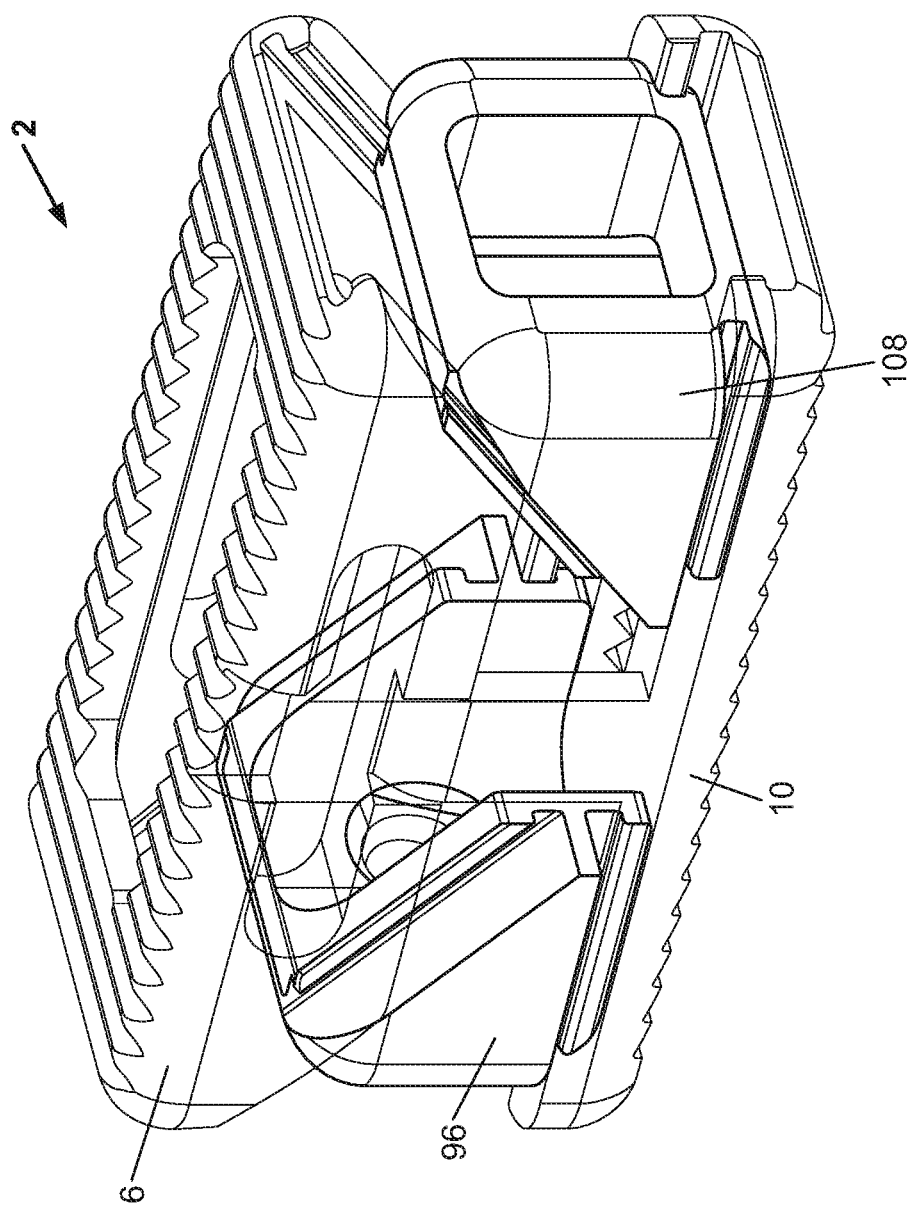
FIGS. 24 and 25 are perspective and top views, respectively, of the variation of the device of FIG. 1 in a deployed configuration.
Figure 25:
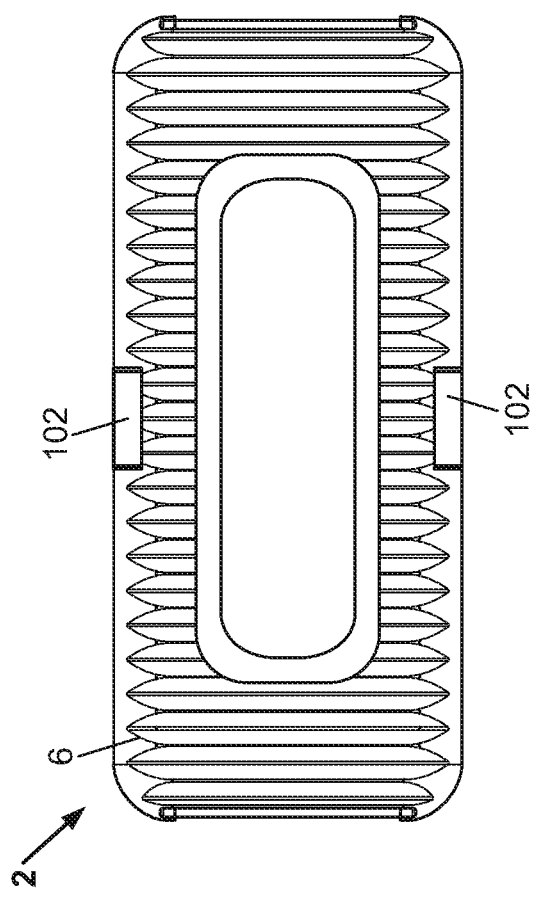

FIGS. 24 and 25 illustrate the device 2 in a deployed configuration, for example after completion of the longitudinal compression 160 and radial and/or vertical expansion as shown in FIG. 23.

Figure 26:
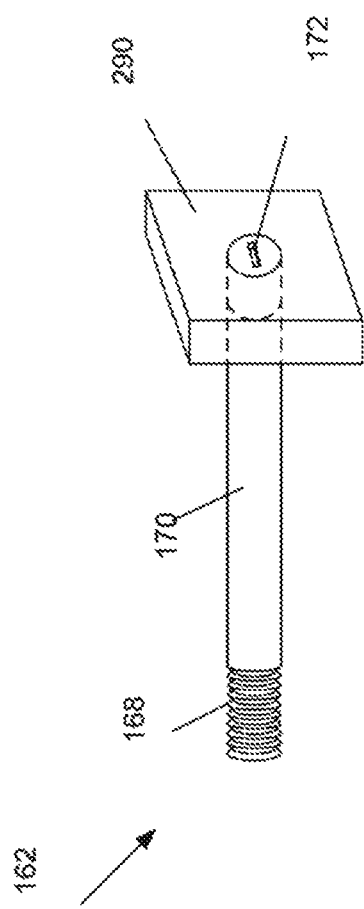

FIG. 26 illustrates a variation of the locking pin 162 that can have a pin shaft 170 with a driver slot 172, for example, configured to receive a screw driver or drill bit. The pin shaft 170 can have pin thread 168 configured to releasably or fixedly attach to one or both of the ramp ports. The pin thread 168 can extend along all or part of the length of the pin shaft 170. The pin shaft 170 can be rotatably or fixedly attached to or integral with a locking plate 290. The locking plate 290 can be at the end of the pin shaft 170 with the driver slot 172. The locking plate 290 can be at the same or opposite end of the pin shaft 170 from the thread.

FIG. 27 illustrates that the pin shaft 170 can have no locking plate 290. The pin thread 168 can be at the end of the pin shaft 170 with the driver slot 172. One end of the pin shaft 170, for example opposite the driver slot 172, can be an abutment end 174.

FIG. 28 illustrates that the locking pin 162 can be inserted, as shown by arrow, through the second side ramp 108. FIG. 29 illustrates that the pin shaft 170 can be translated and rotated, as shown by arrows, to screw the pin thread 168 into the threaded ramp port in the first side ramp 96. The ramp locking plate can fit into the ramp locking plate port 110. The locking pin 162 can be screwed tightly enough to substantially fix the locking pin 162.

FIG. 30 illustrates that the locking pin 162 can be inserted, as shown by arrow, through the threaded ramp port. The second side ramp 108 and/or the top and/or the bottom plates can have a ramp abutment section 180. The ramp abutment section 180 can be configured to interference fit with and/or fixedly attach to the abutment end 174.

FIG. 31 illustrates that the pin shaft 170 can be translated and rotated, as shown by arrows. The abutment end 174 can interference fit and/or fixedly attach to the ramp abutment section 180.

A biocompatible adhesive or epoxy can be applied to the pin thread 168, threaded ramp port, abutment end 174, ramp abutment section 180, or combinations thereof.

FIGS. 32, 33 and 34 illustrate that one, two or more locking pin channels 164 can be defined longitudinally through the device 2. One, two or more locking pins 162 can be inserted in each locking pin channel 164, for example during or after deployment of the remainder of the device 2. The locking pins 162 can prevent overexpansion and/or overcompression and/or disassembly of the device 2.

The locking pin channel 164 can have locking pin ports 166 through the top, and/or bottom plates, and/or either or both side ramps.

Two locking pin channel 164 can be located on opposite sides of the threaded ramp port. The locking pin channels 164 and ports can have a circular cross-section (i.e., be cylindrical), as shown in FIG. 34.

Figure 35:
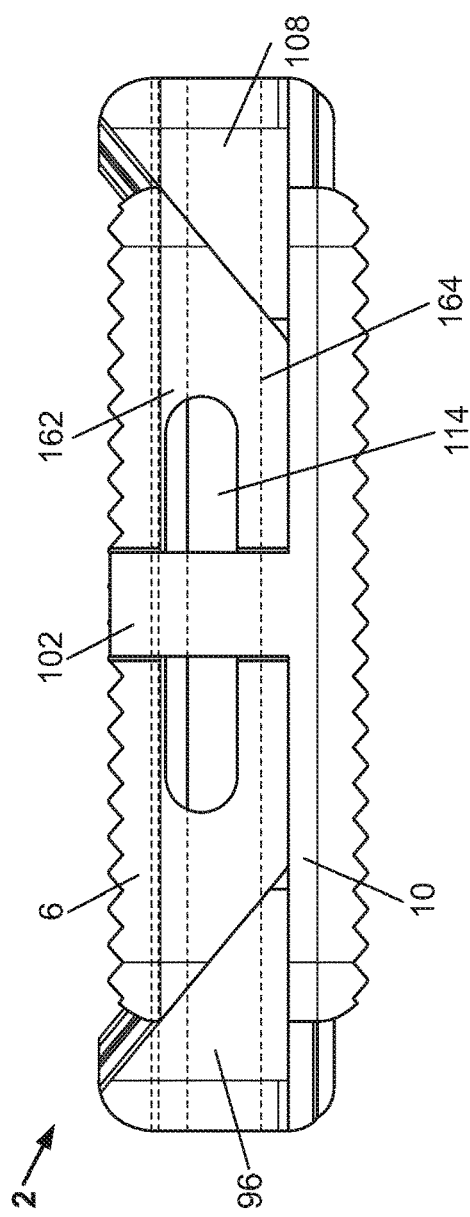
FIGS. 35 and 36 are side and end views, respectively, of a variation of the device with the locking pin.
Figure 36:
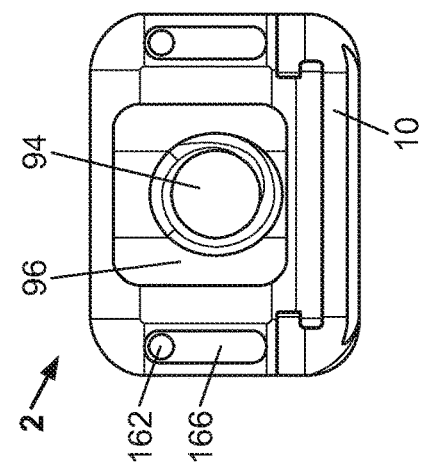

FIGS. 35 and 36 illustrates that the locking pin 162 can be cylindrical. The locking pin channel 164 and locking pin port 166 can have elongated cross-sections, such as an oval or rectangular or oblong cross-sections. The locking pin 162 can be free to move vertically within a range of motion within the locking pin port 166.

Figure 37:
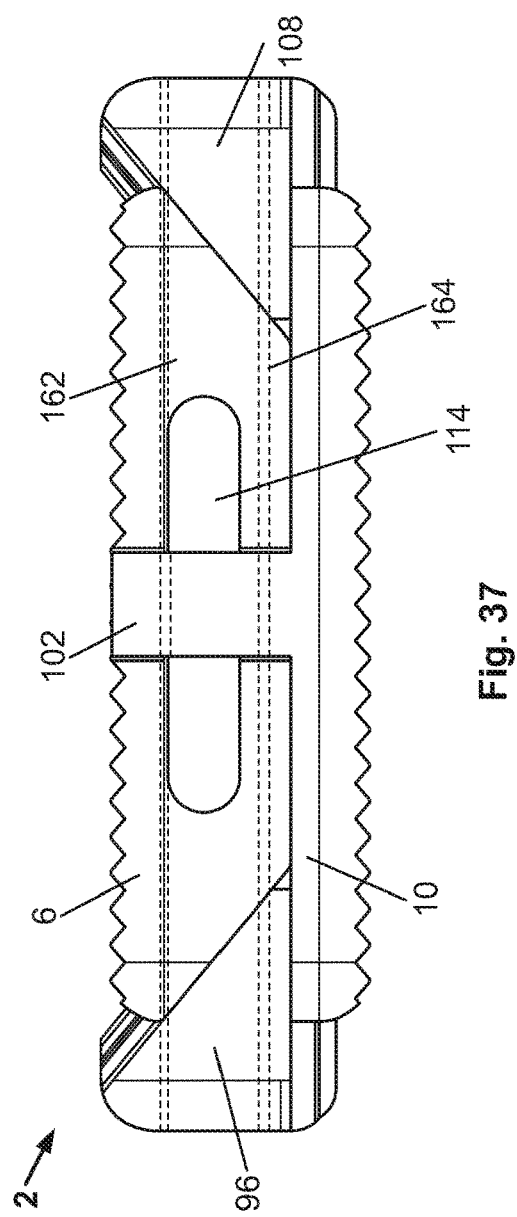
FIGS. 37 and 38 are side and end views, respectively, of a variation of the device with the locking pin.
Figure 38:
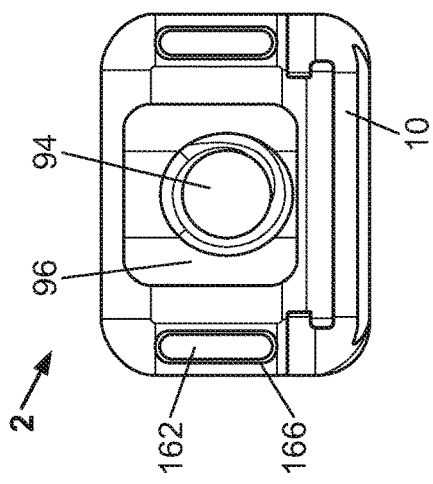

FIGS. 37 and 38 illustrate that the locking pin 162 can be a substantially similar shape and size as the locking pin channel 164. The locking pin 162 can be substantially unmovable within the locking pin port 166. The locking pin 162, locking pin channel 164 and locking pin port 166 can all have elongated cross-sections, such as an oval or rectangular or oblong cross-sections.

One or both of the ramps 22 can have first fixing teeth 192. The first fixing teeth 192 can be in contact with the top and/or the bottom. The top and/or the bottom (shown as bottom only) plates 286 can have second fixing teeth 190.

The first fixing teeth 192 can mechanically interact with the second fixing teeth 190 to allow relative translation in a first direction. The first fixing teeth 192 and the second fixing teeth 190 can interact to obstruct (e.g., by interference fitting the first fixing teeth 192 against the second fixing teeth 190) relative translation in a second direction. For example, the fixing teeth can obstruct the side ramps from moving longitudinally away from each other (i.e., and obstruct the top from moving closer to the bottom). Also for example, the fixing teeth can allow relative translation of the side ramps toward each other (i.e., and allow the top to move away from the bottom).

The second side ramp 108 can have a first end 186. The first end 186 can be configured to dissect tissue. The first end 186 can have a blunt or sharp point.

The second side ramp 108 can have a tool connector 184, such as an externally and/or internally threaded cylinder extending longitudinally from the second side ramp 108 away from the first side ramp 96. The tool connector 184 can be configured to removably attach to a deployment tool 80.

The first side ramp 96 and second side ramp 108 can be longitudinally compressed toward each other. For example, an external deployment tool 80 can be attached to the first side ramp 96 and second side ramp 108 and apply a compressive force. The base 138 and top plates 6 can expand away from each other.

The first fixing teeth 192 can unidirectionally interference fit the second fixing teeth 190. The unidirectional interference fit of the first fixing teeth 192 and the second fixing teeth 190 can substantially impede or prevent the opposite ramps 22 from moving longitudinally away from each other, for example, therefore impede or preventing compression 196 of the top toward the bottom and vice versa.

The unidirectional interference fit of the first fixing teeth 192 and the second fixing teeth 190 can allow the opposite ramps 22 to move longitudinally toward each other, for example, therefore allowing the top to expand away from the bottom and vice versa.

The expandable support devices 188 can have textured and/or porous surfaces for example, to increase friction against bone surfaces, and/or promote tissue ingrowth. The expandable support devices 188 can be coated with a bone growth factor, such as a calcium base 138.

Figure 39A:
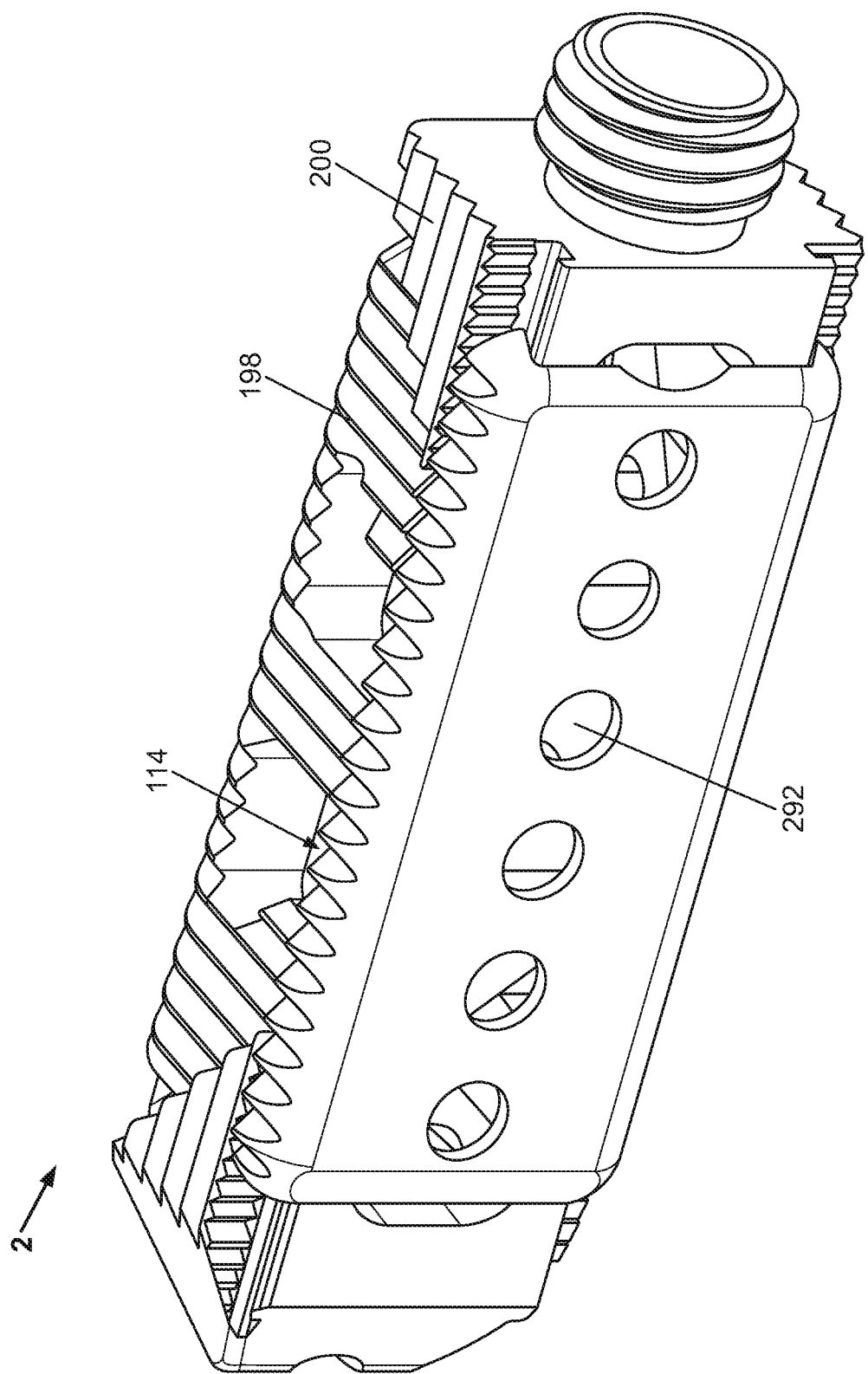
FIGS. 39a, 39b and 39c are bottom perspective, end and side views, respectively, of a variation of the device in a longitudinally expanded configuration.
Figure 39B:
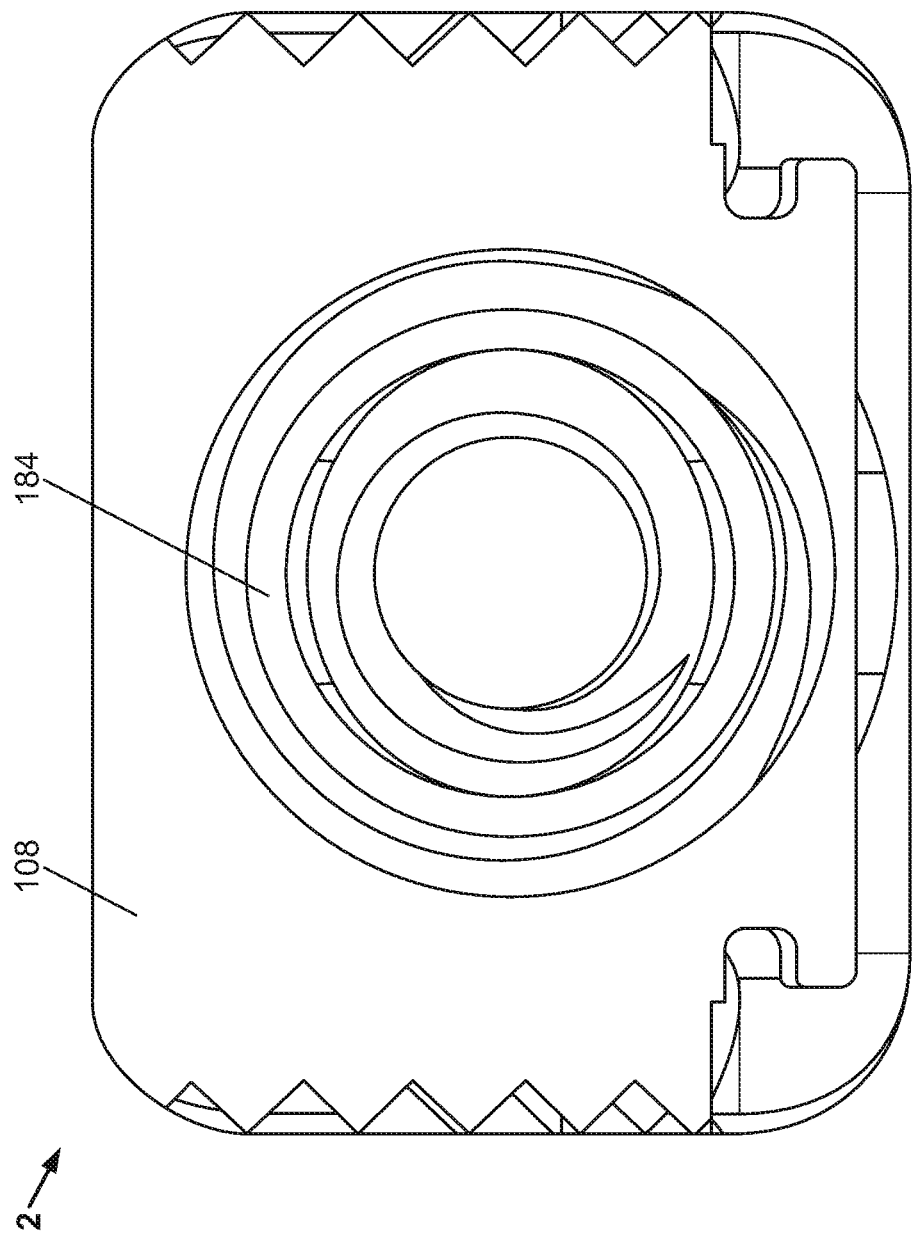
Figure 39C:
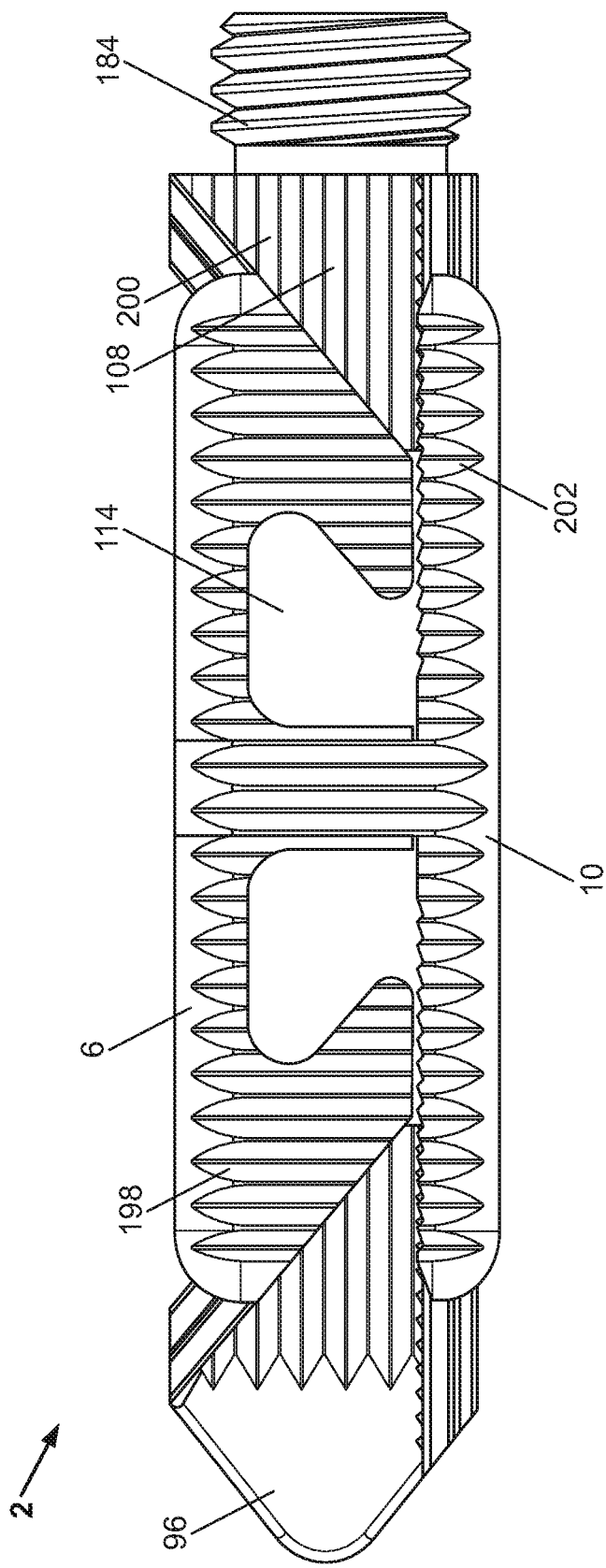

FIGS. 39a through 39c illustrate that the bottom ports can be one or more circular ports, for example six ports. The bottom ports can be aligned in a single row parallel with the longitudinal axis of the device 2.

The side ports 114 can open against the edge of the top plate 6 on one or more sides (e.g., the bottom sides, as shown) of the side ports 114.

The top plate 6 can have top plate side teeth 198 on the external lateral sides of the top plate 6. The bottom plate 10 can have bottom plate side teeth 202 on the external lateral sides of the bottom plate. The top plate side teeth 198 and/or the bottom plate side teeth 202 can be oriented from the top to the bottom of the device 2 (i.e., perpendicular to the longitudinal axis of the device 2). The top plate side teeth 198 can be aligned with the bottom plate side teeth 202.

The external lateral sides of the first side ramp 96 and/or second side ramp 108 can have ramp side teeth 200. The ramp side teeth 200 can be oriented parallel with the longitudinal axis of the device 2. The top plate side teeth 198 and/or the bottom plate side teeth 202 can be oriented perpendicular to the orientation of the ramp side teeth 200.

Figure 40A:
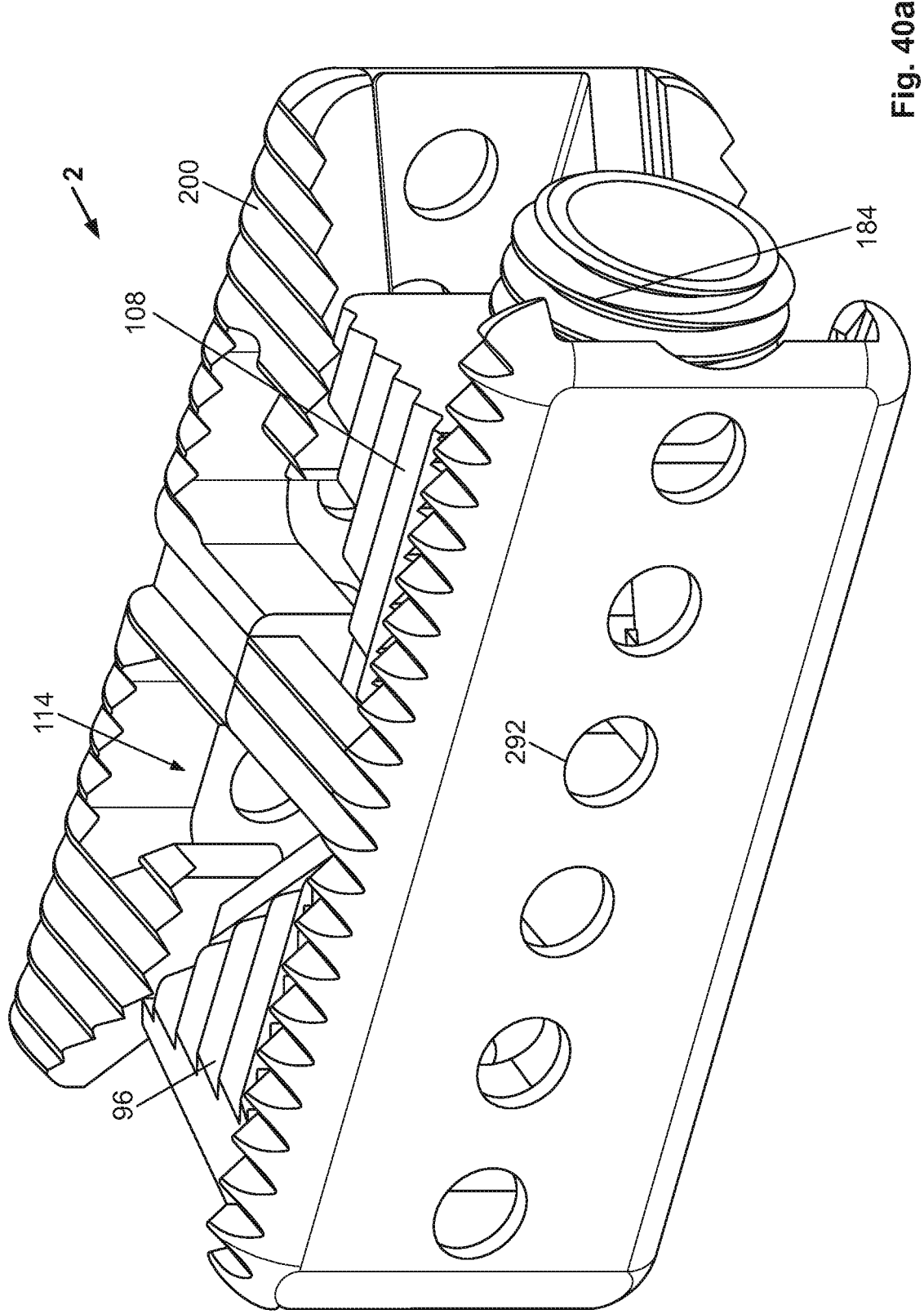
FIGS. 40a, 40b, and 40c are bottom perspective, end and side views, respectively, of the device of FIGS. 39a through 39c in a longitudinally compressed and radially expanded configuration.
Figure 40B:
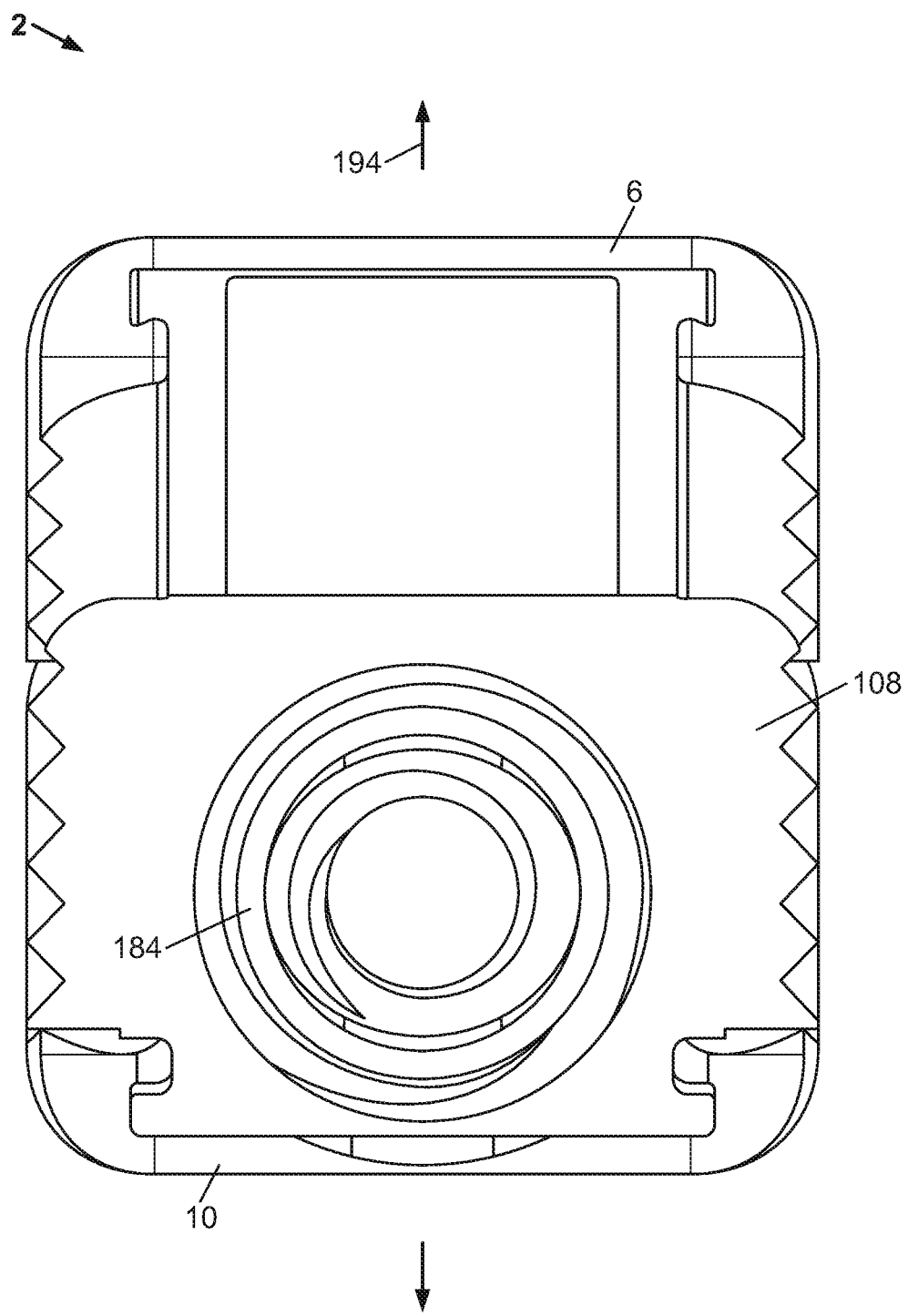
Figure 40C:
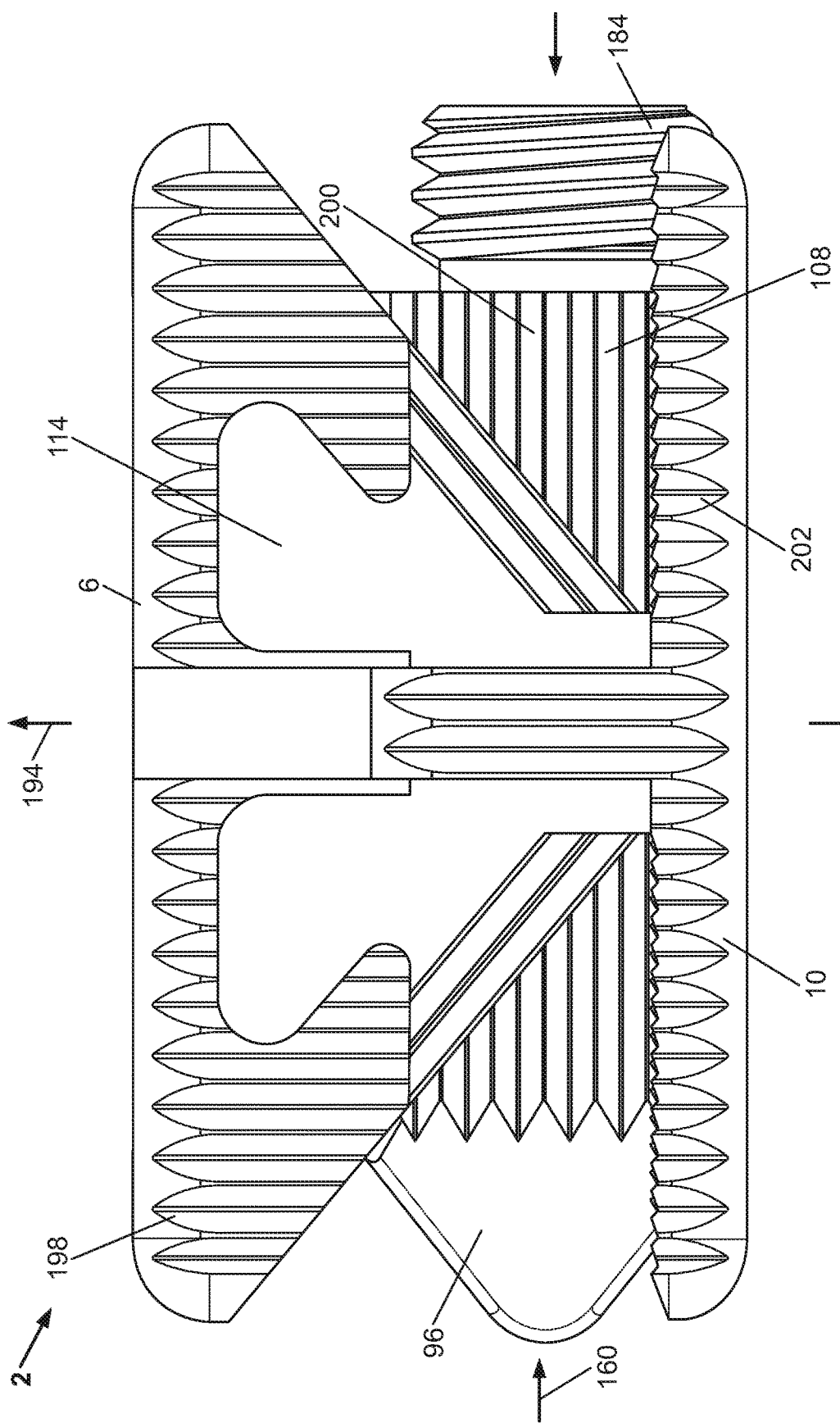

FIGS. 40a through 40c illustrate that the top plate 6 and/or bottom plate 10 can be expanded away from each other in the directions of the orientation of the longitudinal axes of the top plate side teeth 198 and the bottom plate side teeth 202. The first and/or second side ramps 108 can be contracted toward one another in the direction of the orientation of the longitudinal axis of the ramp side teeth 200 of the first and second side ramps 108. The top plate side teeth 198, bottom plate side teeth 202, and ramp side teeth 200 can act as low-friction rails 42 against surrounding tissue when the device 2 is radially expanded at the target site 264.

The side ports 114 that open to the bottom edge of the top plate 6 can create a single side port 114 that can extend to the bottom plate.

The plates 286 and wedges 18 can be rigid or exhibit ductile or deformable expansion 92 during deployment. The transverse cross-section of the device 2 can be non-round. For example, The device 2 can have a square or rectangular transverse cross-section. The device 2 can have a substantially triangular or quadrilateral (e.g., trapezoidal) cross-section. The device 2 can have a round, hexagonal, octagonal, or other transverse cross-sectional configuration.

The device 2 can have one or more radiopaque and/or echogenic markers. For example, the device 2 can have aligned markers on the top plate 6, middle plate 8 and bottom plate. When the device 2 is in a contracted pre-deployment configuration, the markers can be located immediately adjacent to one another, for example appearing as a single marker. When the device 2 is in an expanded configuration, the markers can move apart from each other, indicating to a doctor performing the implantation and deployment procedure using visualization (e.g., x-ray or ultrasound-based) that the device 2 has expanded. Under visualization the markers can also indicate the location and orientation of the device 2.

Method of Using

The devices can be made from PEEK, any medical grade polymer or metal, or any other material disclosed herein. For example, the side ramps can be made from titanium and/or a titanium alloy and the bottom and/or top plates can be made from PEEK. The device can be coated, for example with bone morphogenic protein (BMP), ceramic, and/or any other material disclosed herein, before, during or after deployment into the target site. The device can be deployed less (e.g., minimally) invasively, over the wire, percutaneously, used with a vertebral body replacement or fusion cage, or combinations thereof. The device can be expandable and un-expandable for removal or repositioning.

Figure 41:
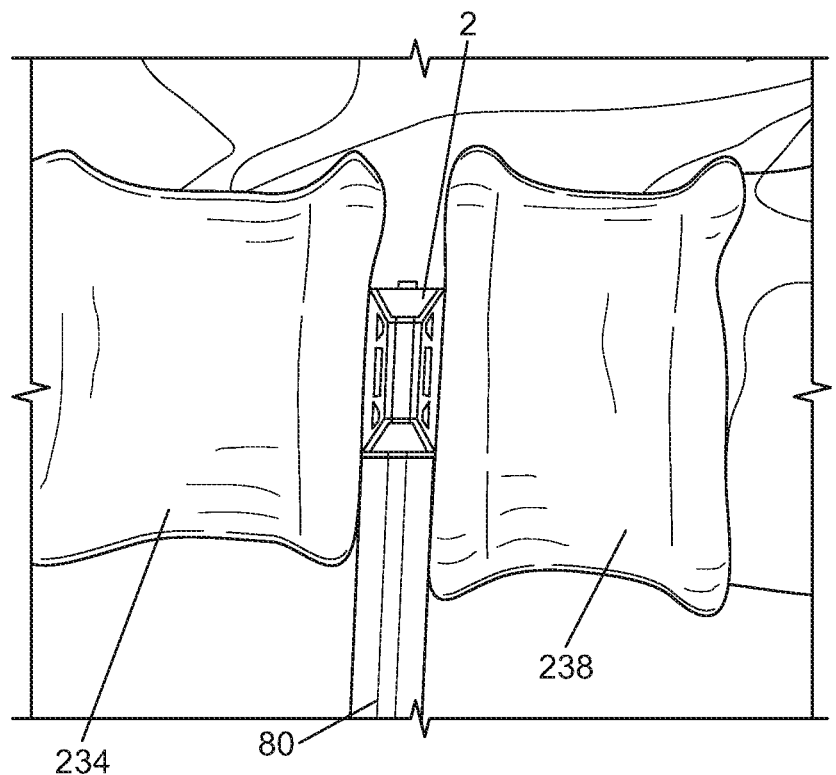
FIG. 41 illustrates a visualization of a variation of a method for deploying the device into the spine between adjacent vertebrae.

FIG. 41 illustrates that the device can be removably attached to a delivery system or deployment tool. The deployment tool can insert the device into the target site. For example the deployment tool can be pushed over a guidewire.

When the device is positioned as desired (e.g., between adjacent vertebral plates) and expanded and/or locked, the deployment tool can then be releases from the device. The device can be configured to lock itself into place with outward expansion, wedging, or interference force when receiving a release force from the deployment tool or otherwise. For example, the device can have unidirectionally sliding teeth oppositely located on the adjacent surfaces of the wedges and plates.

A leader or wire, such as a guidewire, can be inserted or otherwise deployed into the target site, for example, the wire can be percutaneously inserted in a minimally invasive procedure. The wire can be inserted into the intervertebral space, for example between a first vertebral plate and an adjacent, second, vertebral plate. The wire can be anteriorly and/or posteriorly inserted. The wire can be laterally inserted.

Whether or not the device is inserted over or along the wire, the device can be inserted into the target site (e.g., between adjacent vertebral bodies) from an anterior, lateral, posterior, transforaminal approach, or combinations thereof.

FIG. 41 illustrates the deployment tool inserted to a target site in vivo between a first vertebra and a second vertebra. For example, the device can be placed at the target site after a partial or complete discectomy. When the device is in a contracted configuration, the tool can position the device between a first vertebral body of the first vertebra and a second vertebral body of the second vertebra. The device can be inserted into the target site a direction substantially parallel to the surfaces of the vertebral body end plates. The device can be placed between a first vertebral end plate of the first vertebral body and the adjacent second vertebral end plate of the second vertebral body. In this inter-vertebral location, the top plate of the device can be in contact with or directly adjacent to the first vertebral end plate. The bottom plate of the device can be in contact with or directly adjacent to the second vertebral end plate.

Figure 42A:
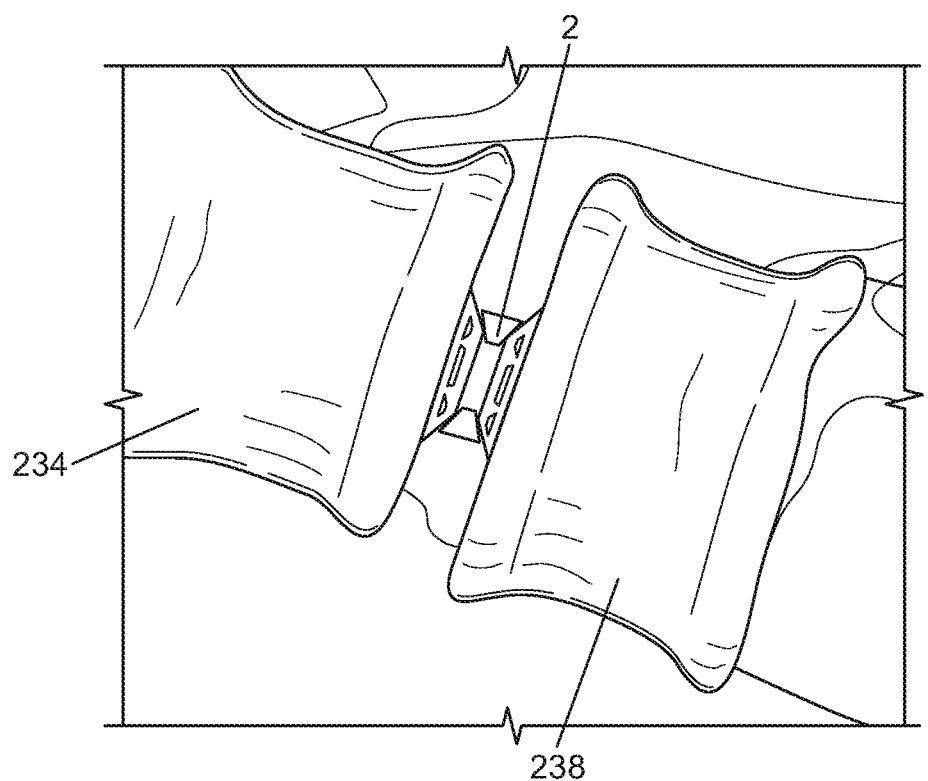
FIGS. 42a and 42b illustrate visualizations of variations of the device deployed into the spine between adjacent vertebrae.
Figure 42B:
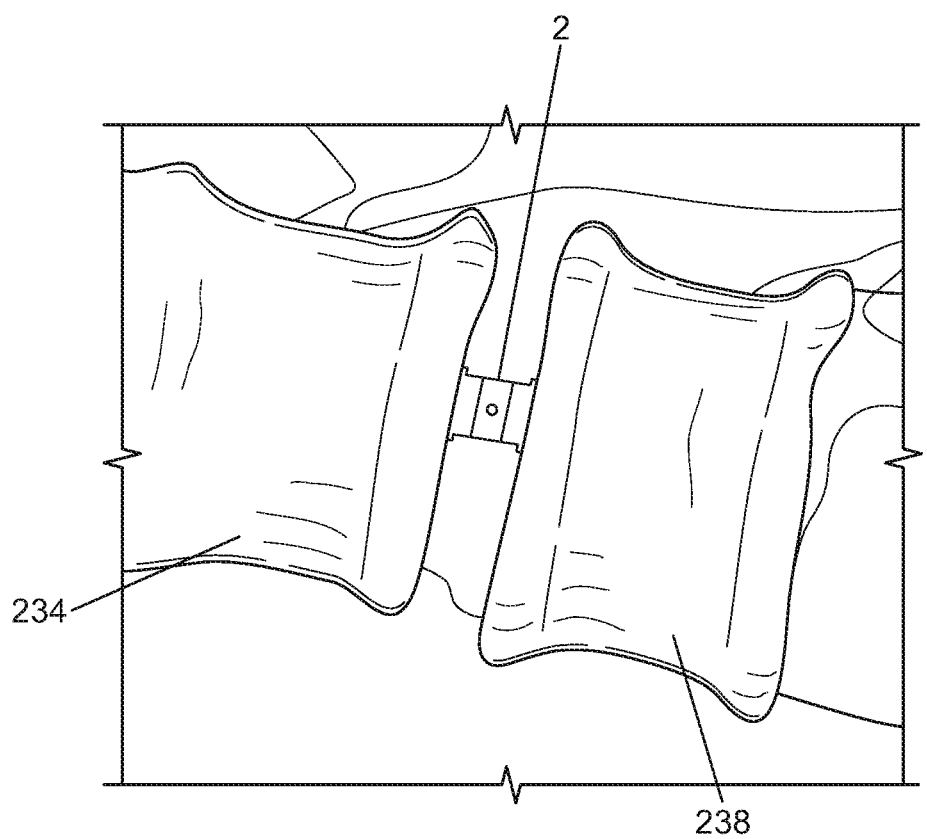

FIGS. 42a and 42b illustrate that the deployment tool can radially expand the device between the first vertebral end plate and the second vertebral end plate. The top plate can press against and/or embed into the first vertebral end plate. The bottom plate can press against and/or embed into the second vertebral end plate. The device can fuse the first vertebra to the second vertebra.

The device can be filled with a filled before or after radial expansion. Tissue ingrowth can occur into the top plate through the top ports, bottom plate through the bottom ports, and elsewhere through the device.

The device can provide fusion between the adjacent vertebrae. The devices can have radiopaque and/or echogenic visualization markers, for example the markers can be along the top plate, bottom plate, and one or more panels of the plates. The deployment tool can also have one or more markers. The devices can be inserted into multiple interbody target sites of the spine to provide fusion between adjacent vertebral bodies. A first device can be inserted into a first interbody site and a second device can be inserted into a second interbody site. The first and second devices can be inserted bilaterally, for example both devices can be inserted between the same first vertebra and second vertebra from opposite lateral sides.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEY), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The device can be made from substantially 100% PEEK, substantially 100% titanium or titanium alloy, or combinations thereof.

Any or all elements of the device and/or other devices or apparatuses described herein, can be, have, and/or be completely or partially coated with agents for cell ingrowth.

The device and/or elements of the device and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rh-BMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor choline; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin;

mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostaglandin $E_2$ Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

I claim:

1. A method of using an orthopedic support device comprising:
    positioning the device at a target site, wherein the device has a longitudinal axis, and wherein the device comprises a first plate, a second plate opposite to the first plate, a lateral panel that forms at least part of a lateral-facing exterior surface of the device, a first wedge between the first plate and the second plate at a first end of the device, a second wedge between the first plate and the second plate at a second end of the device, and a tool connector having threads and a driver slot for receiving a non-threaded actuating driver, wherein the driver slot has an open proximal end and a closed distal end, wherein the first plate has a first extension extending in the direction of the second plate, and wherein the second plate has a second plate receiver configured to receive the first extension;
    expanding the device at the target site, wherein expanding the device comprises longitudinally moving the first wedge and the second wedge coplanarly toward the longitudinal middle of the device, and wherein the expanding comprises moving the second plate away from the first plate along a first dimensional axis, and wherein expanding further comprises moving the second plate farther away from a surface of the first wedge in contact with the first plate, and wherein expanding further comprises moving the second plate farther away from a surface of the second wedge in contact with the first plate, and wherein the first extension remains in a constant position with respect to the first wedge in the direction of the first dimensional axis, and wherein the tool connector translates between the first plate and the second plate during the expansion of the device, and wherein the first extension slides in the second plate receiver during the expansion of the device.

2. The method of claim 1, wherein expanding further comprises restricting a longitudinal translation between the first plate and the second plate.

3. The method of claim 2, wherein the lateral panel is attached to and extends from the second plate, and wherein the restricting the longitudinal translation between the first plate and the second plate comprises sliding of the first extension in the second plate receiver.

4. The method of claim 1, further comprising inserting a locking element into the device wherein the locking element is configured to prevent a change in the vertical dimension of the device.

5. The method of claim 1, wherein expanding further comprises rotating an elongated element positioned along the longitudinal axis.

6. The method of claim 1, wherein expanding further comprises rotating an elongated element parallel to at least one of the first plate and/or the second plate.

7. The device of claim 1, wherein the tool connector has a constant length during the expansion of the device.

8. The device of claim 1, wherein the tool connector has an exposed threaded portion that extends longitudinally from the second wedge, away from the first wedge.

9. The device of claim 1, wherein the closed distal end of the driver slot is defined by a surface at a longitudinal center of the driver slot.

10. The device of claim 1, wherein when the non-threaded actuating driver is engaged with the driver slot, the non-threaded actuating driver is in a longitudinal center of the driver slot along the longitudinal axis of the device.

11. The device of claim 1, wherein the first configuration is a device unexpanded configuration, wherein the second configuration is a device expanded configuration, and wherein the driver slot is a proximal-most cavity of the device when the device is in the device unexpanded configuration and when the device is in the device expanded configuration.

* * * * *